United States Patent
Termin et al.

(10) Patent No.: US 7,297,708 B2
(45) Date of Patent: Nov. 20, 2007

(54) HETEROAROMATIC SUBSTITUTED CYCLOPROPANE AS CORTICOTROPIN RELEASING HORMONE LIGANDS

(75) Inventors: Andreas Termin, Encinitas, CA (US); Peter D. J. Grootenhuis, San Diego, CA (US); Dean M. Wilson, San Diego, CA (US); Valentina Molteni, San Diego, CA (US); Long Mao, San Diego, CA (US); Angelo Castellino, San Diego, CA (US); Zhicai Yang, Schenectady, NY (US); Anthony Pechulis, Niskayuna, NY (US); Mark Suto, La Jolla, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 831 days.

(21) Appl. No.: 10/235,436

(22) Filed: Sep. 5, 2002

(65) Prior Publication Data
US 2003/0229091 A1 Dec. 11, 2003

Related U.S. Application Data
(60) Provisional application No. 60/317,529, filed on Sep. 6, 2001.

(51) Int. Cl.
*A61K 31/4164* (2006.01)
*C07D 233/54* (2006.01)

(52) U.S. Cl. .............. 514/396; 544/242; 544/336; 546/268.1; 546/272.7; 548/335.1; 548/343.1; 548/343.5; 514/397

(58) Field of Classification Search ............ 548/335.1, 548/343.5, 343.1; 514/396; 544/242, 336; 546/268.1
See application file for complete search history.

(56) References Cited

U.S. PATENT DOCUMENTS 6,444,687 B1 * 9/2002 Stamford et al. ............ 514/318
6,559,172 B1 * 5/2003 Heerding et al. ............ 514/396
6,632,828 B2 * 10/2003 Stamford et al. ............ 514/333

* cited by examiner

*Primary Examiner*—Golam M M Shameem
(74) *Attorney, Agent, or Firm*—Shah R. Makujina

(57) ABSTRACT

Provided herein are novel heteroaromatic substituted cyclopropanes of the Formula (I):

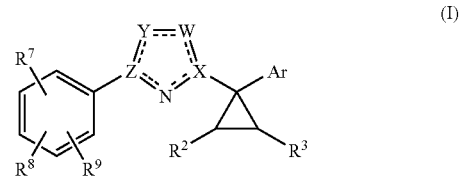

as well as compositions, including pharmaceutical compositions, containing the same, and the use thereof in the treatment of various neurological and psychological disorders, e.g., anxiety and depression, treatable by antagonizing CRF receptors.

8 Claims, No Drawings

HETEROAROMATIC SUBSTITUTED CYCLOPROPANE AS CORTICOTROPIN RELEASING HORMONE LIGANDS

CROSS-REFERENCE TO RELATED APPLICATIONS

This application claims the priority benefit of U.S. Provisional Application No. 60/317,529, filed Sep. 6, 2001, the disclosure of which is incorporated herein by reference in its entirety.

FIELD OF THE INVENTION

This invention relates to compounds which are novel heteroaromatic substituted cyclopropanes, and to the use of such compounds as CRF receptor ligands in the treatment of various CRF-related disorders.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad. Sci. (USA) 80:4851 (1983); W. Vale et al., Science 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebrospinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Rol5-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-helical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome, post-operative ileus and colonic hypersensitivity associated with psychopathological disturbance and stress [for reviews see E. D. DeSouza, C. B. Nemeroff, Editors; Corticotropin-Releasing Factor: Basic and Clinical Studies of a Neuropeptide, E. B. De Souza and C. B. Nemeroff eds., CRC Press p221 (1990) and C. Maillot, M. Million, J. Y. Wei, A. Gauthier, Y. Tache, Gastroenterology, 119, 1569-1579 (2000)].

Over-expression or under-expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress [for reviews see J. R. McCarthy, S. C. Heinrichs and D. E. Grigoriadis, Cuur. Pharm. Res., 5, 289-315 (1999); P. J. Gilligan, D. W. Robertson and R. Zaczek, J. Medicinal Chem., 43, 1641-1660 (2000), G. P. Chrousos, Int. J. Obesity, 24, Suppl. 2, S50-S55 (2000); E. Webster, D. J. Torpy, I. J. Elenkov, G. P. Chrousos, Ann. N.Y. Acad. Sci., 840, 21-32 (1998); D. J. Newport and C. B. Nemeroff, Curr. Opin. Neurobiology, 10, 211-218 (2000); G. Mastorakos and I. Ilias, Ann. N.Y. Acad. Sci., 900, 95-106 (2000); M. J. Owens and C. B. Nemeroff, Expert Opin. Invest. Drugs, 8, 1849-1858 (1999); G. F. Koob, Ann. N.Y. Acad. Sci., 909, 170-185 (2000)].

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; WO00/01675; and U.S. Ser. No 10/192,055.

SUMMARY OF THE INVENTION

In accordance with one aspect, the present invention provides novel compounds of Formulae (I)-(Ie) described below, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post- traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal.

The present invention provides novel compounds of Formulae (I)-(Ie) described below which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

According to another aspect, the present invention provides novel compounds of Formulae (I)-(Ie) which are useful as antagonists of the corticotropin releasing factor. The compounds of the present invention exhibit activity as corticotropin releasing factor antagonists and can suppress CRF hypersecretion. The present invention also includes pharmaceutical compositions containing such compounds of Formulae (I)-(Ie) and methods of using such compounds for the suppression of CRF hypersecretion, and/or for the treatment of anxiogenic disorders.

According to yet another aspect of the invention, the compounds of Formulae (I)-(Ie) provided by this invention (and especially labelled compounds of this invention) are also useful as standards and reagents in determining the ability of a potential pharmaceutical to bind to the CRF receptor.

DETAILED DESCRIPTION OF THE INVENTION

This invention is a class of novel compounds which are CRF receptor ligands and which can be represented by Formula (I):

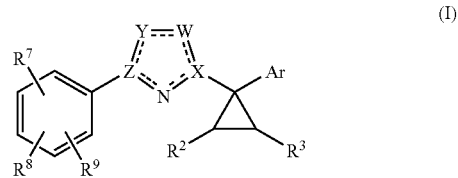

or a pharmaceutically acceptable salt forms thereof, wherein:

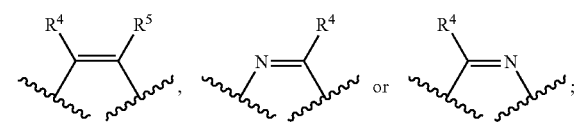

W is $CR^6$, $NR^6$,
X is C or N;
Y is $CR^1$ or N;

Z is C or N;

R$^1$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{13}$, CH$_2$NR$^{13}$R$^{14}$, —CH$_2$OH, —NO$_2$, $C_3$-$C_6$ cycloalkyl, —NR$^{13}$R$^{14}$, —NR$^{13}$COR$^{14}$, —NHSO$_2$R, —COR$^{13}$, —CO$_2$R$^{13}$, —OR$^{13}$, —OC$_2$H$_4$OR$^{13}$, —SR$^{13}$, —S(O)$_n$R$^{13}$, —S(O)$_n$NR$^{13}$R$^{14}$, —CH(OH)R$^{13}$, —CH$_2$COR$^{13}$, —OC(O)R$^{13}$, —OCHR$^{13}$CO$_2$R$^{14}$, —OCHR$^{13}$COR$^{14}$, —NR$^{13}$CONR$^{13}$R$^{14}$, —NR$^{13}$CO$_2$R$^{14}$, —CONR$^{13}$R$^{14}$, or —CH(OH)C(R$^{13}$)$_3$;

R$^2$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{15}$, CH$_2$NR$^{15}$R$^{16}$, —CH$_2$OH, —NO$_2$, $C_3$-$C_6$ cycloalkyl, —NR$^{15}$R$^{16}$, —NR$^{15}$COR$^{16}$, —NHSO$_2$R, —COR$^{15}$, —CO$_2$R$^{15}$, —OR$^{15}$, —OC$_2$H$_4$OR$^{15}$, —SR$^{15}$, —S(O)$_n$R$^{15}$, —S(O)$_n$NR$^{15}$R$^{16}$, —CH(OH)R$^{15}$, —CH$_2$COR$^{15}$, —OC(O)R$^{15}$, —OCHR$^{15}$CO$_2$R$^{16}$, —OCHR$^{15}$COR$^{16}$, —NR$^{15}$CONR$^{15}$R$^{16}$, —NR$^{15}$CO$_2$R$^{16}$, —CONR$^{15}$R$^{16}$, or —CH(OH)C(R$^{15}$)$_3$;

R$^3$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{17}$, CH$_2$NR$^{17}$R$^{18}$, —CH$_2$OH, —NO$_2$, $C_3$-$C_6$ cycloalkyl, —NR$^{17}$R$^{18}$, —NR$^{17}$COR$^{18}$, —NHSO$_2$R, —COR$^{17}$, —CO$_2$R$^{17}$, —OR$^{17}$, —OC$_2$H$_4$OR$^{17}$, —SR$^{17}$, —S(O)$_n$R$^{17}$, —S(O)$_n$NR$^{17}$R$^{18}$, —CH(OH)R$^{17}$, —CH$_2$COR$^{17}$, —OC(O)R$^{17}$, —OCHR$^{17}$CO$_2$R$^{18}$, —OCHR$^{17}$COR$^{18}$, —NR$^{17}$CONR$^{17}$R$^{18}$, —NR$^{17}$CO$_2$R$^{18}$, —CONR$^{17}$R$^{18}$, or —CH(OH)C(R$^{17}$)$_3$;

each R$^4$ and R$^5$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{19}$, CH$_2$NR$^{19}$R$^{20}$, —CH$_2$OH, —NO$_2$, $C_3$-$C_6$ cycloalkyl, —NR$^{19}$R$^{20}$, —NR$^{19}$COR$^{20}$, —NHSO$_2$R, —COR$^{19}$, —CO$_2$R$^{19}$, —OR$^{19}$, —OC$_2$H$_4$OR$^{19}$, —SR$^{19}$, —S(O)$_n$R$^{19}$, —S(O)$_n$NR$^{19}$R$^{20}$, —CH(OH)R$^{19}$, —CH$_2$COR$^{19}$, —OC(O)R$^{19}$, —OCHR$^{19}$CO$_2$R$^{20}$, OCHR$^{19}$COR$^{20}$, —NR$^{19}$CONR$^{19}$R$^{20}$, —NR$^{19}$CO$_2$R$^{20}$, CONR$^{19}$R$^{20}$, or —CH(OH)C(R$^{19}$)$_3$;

R$^6$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{21}$, CH$_2$NR$^{21}$R$^{22}$, —CH$_2$OH, —NO$_2$, $C_3$-$C_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^7$, R$^8$ and R$^9$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$;

each R$^{10}$ is, independently, H, halogen, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy, aryl, heteroaryl or heterocyclyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO2R$^{24}$, —CONR$^{23}$R$^{24}$, or —CH(OH)C(R$^{23}$)$_3$, wherein each alkyl, haloalkyl, or cycloalkyl is optionally substituted with one or more groups independently selected from halogen, hydroxyl, or —CN;

each R$^{11}$ and R$^{12}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{13}$ and R$^{14}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{15}$ and R$^{16}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{17}$ and R$^{18}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{19}$ and R$^{20}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{21}$ and R$^{22}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{23}$ and R$^{24}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

Ar is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl 3,4-dihydro-2H-benzo[1,4]oxazine, benzo[1,3]dioxole, or heterocyclyl, wherein said Ar is optionally substituted with 1 to 5 R$^{10}$;

n is 0-2;

aryl is phenyl, benzyl or naphthyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —COR$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$; and heterocyclyl is optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$.

Other embodiments of the present invention include compounds of Formula (Ia):

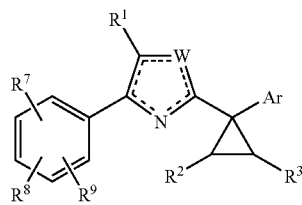

(Ia)

or a pharmaceutically acceptable salt forms thereof, wherein:

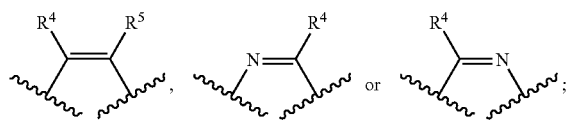

$R^1$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{13}$, CH$_2$NR$^{13}$R$^{14}$, —CH$_2$OH, —NO$_2$, $C_3$-$C_6$ cycloalkyl, —NR$^{13}$R$^{14}$, —NR$^{13}$COR$^{14}$, —NHSO$_2$R, —COR$^{13}$, —C$_2$R$^{13}$, —OR$^{13}$, —OC$_2$H$_4$OR$^{13}$, —SR$^{13}$, —S(O)$_n$R$^{13}$, —S(O)$_n$NR$^{13}$R$^{41}$, —CH(OH)R$^{13}$, —CH$_2$COR$^{13}$, —OC(O)R$^{13}$, —OCHR$^{13}$CO$_2$R$^{14}$, —OCHR$^{13}$COR$^{14}$, —NR$^{13}$CONR$^{13}$R$^{14}$, —NR$^{13}$CO$_2$R$^{14}$, —CONR$^{13}$R$^{14}$, or —CH(OH)C(R$^{13}$)$_3$;

$R^2$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{15}$, CH$_2$NR$^{15}$R$^{16}$, —CH$_2$OH, —NO$_2$, $C_3$-$C_6$ cycloalkyl, —NR$^{15}$R$^{16}$, —NR$^{15}$COR$^{16}$, —NHSO$_2$R, —COR$^{15}$, —CO$_2$R$^{15}$, —OR$^{15}$, —OC$_2$H$_4$OR$^{15}$, —SR$^{15}$, —S(O)$_n$R$^{15}$, —S(O)$_n$NR$^{15}$R$^{16}$, —CH(OH)R$^{15}$, —CH$_2$COR$^{15}$, —OC(O)R$^{15}$, —OCHR$^{15}$CO$_2$R$^{16}$, —OCHR$^{15}$COR$^{16}$, —NR$^{15}$CONR$^{15}$R$^{16}$, —NR$^{15}$CO$_2$R$^{16}$, —CONR$^{15}$R$^{16}$, or —CH(OH)C(R$^{15}$)$_3$;

$R^3$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{17}$, CH$_2$NR$^{17}$R$^{18}$, —CH$_2$OH, —NO$_2$, $C_3$-$C_6$ cycloalkyl, —NR$^{17}$R$^{18}$, —NR$^{17}$COR$^{18}$, —NHSO$_2$R, —COR$^{17}$, —CO$_2$R$^{17}$, —OR$^{17}$, —OC$_2$H$_4$OR$^{17}$, —SR$^{17}$, —S(O)$_n$R$^{17}$, —S(O)$_n$NR$^{17}$R$^{18}$, —CH(OH)R$^{17}$, —CH$_2$COR$^{17}$, —OC(O)R$^{17}$, OCHR$^{17}$CO$_2$R$^{18}$, —OCHR$^{17}$COR$^{18}$, —NR$^{17}$CONR$^{17}$R$^{18}$, NR$^{17}$CO$_2$R$^{18}$, —CONR$^{17}$R$^{18}$, or —CH(OH)C(R$^{17}$)$_3$;

each $R^4$ and $R^5$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{19}$, CH$_2$NR$^{19}$R$^{20}$, —CH$_2$OH, —NO$_2$, $C_3$-$C_6$ cycloalkyl, —NR$^{19}$R$^{20}$, —NR$^{19}$COR$^{20}$, —NHSO$_2$R, —COR$^{19}$, —CO$_2$R$^{19}$, —OR$^{19}$, —OC$_2$H$_4$OR$^{19}$, —SR$^{19}$, —S(O)$_n$R$^{19}$, —S(O)$_n$NR$^{19}$R$^{20}$, —CH(OH)R$^{19}$, —CH$_2$COR$^{19}$, —OC(O)R$^{19}$, —OCHR$^{19}$CO$_2$R$^{20}$, —OCHR$^{19}$COR$^{20}$, —NR$^{19}$CONR$^{19}$R$^{20}$, —NR$^{19}$CO$_2$R$^{20}$, —CONR$^{19}$R$^{20}$, or —CH(OH)C(R$^{19}$)$_3$;

$R^6$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{21}$, CH$_2$NR$^{21}$R$^{22}$, —CH$_2$OH, —NO$_2$, $C_3$-$C_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, NR$^{21}$CO$_2$R$^{22}$, —CONR$^{21}$R$^{22}$, or —CH(OH)C(R$^{21}$)$_3$;

each $R^7$, $R^8$ and $R^9$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$;

each R is, independently, H, halogen, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy, aryl, heteroaryl or heterocyclyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$, wherein each alkyl, haloalkyl, or cycloalkyl is optionally substituted with one or more groups independently selected from halogen, hydroxyl, or —CN;

each $R^{11}$ and $R^{12}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{13}$ and $R^{14}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{15}$ and $R^{16}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{17}$ and $R^{18}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{19}$ and $R^{20}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{21}$ and $R^{22}$ is, independently, selected at each occurrence from a group consisting essentially of H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, —CN;

each $R^{23}$ and $R^{24}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, —CN;

Ar is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl 3,4-dihydro-2H-benzo[1,4]oxazine, benzo[1,3]dioxole, or heterocyclyl, wherein said Ar is optionally substituted with 1 to 5 $R^{10}$;

n is 0-2;

aryl is phenyl, benzyl or naphthyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-$C_6$ cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^{11}R^{12}$, —$NR^{11}CO_2R^{12}$, —$CONR^{11}R^{12}$, and —$CH(OH)C(R^{11})_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-C6 cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^{11}R^{12}$, —$NR^{11}CO_2R^{12}$, —$CONR^{11}R^{12}$, and —$CH(OH)C(R^{11})_3$; and heterocyclyl is optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-$C_6$ cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^{11}R^{12}$, —$NR^{11}CO_2R^{12}$, —$CONR^{11}R^{12}$, and —$CH(OH)C(R^{11})_3$.

Further embodiments of the present invention include compounds of Formula (Ib):

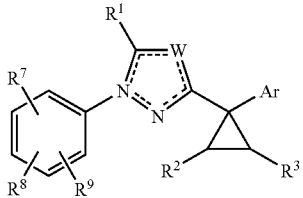

(Ib)

or a pharmaceutically acceptable salt forms thereof, wherein:

W is $CR^6$, $NR^6$,

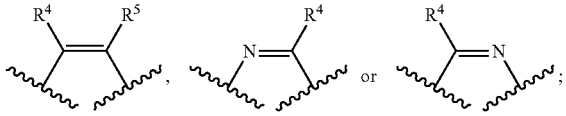

$R^1$ is H, halogen, aryl, heteroaryl, heterocyclyl, $C_1$-$C_6$ alkyl, $C_1$-$C_6$ haloalkyl, $C_2$-$C_6$ alkenyl, $C_2$-C6 alkynyl, —CN, —$CH_2CN$, —$CH_2OR^{13}$, $CH_2NR^{13}R^{14}$, —$CH_2OH$, —$NO_2$, $C_3$-$C_6$ cycloalkyl, —$NR^{13}R^{14}$, —$NR^{13}COR^{14}$, —$NHSO_2R$, —$COR^{13}$, —$CO_2R^{13}$, —$OR^{13}$, —$OC_2H_4OR^{13}$, —$SR^{13}$, —$S(O)_nR^{13}$, —$S(O)_nNR^{13}R^{14}$, —$CH(OH)R^{13}$, —$CH_2COR^{13}$, —$OC(O)R^{13}$, —$OCHR^{13}CO_2R^{14}$, —$OCHR^{13}COR^{14}$, —$NR^{13}CONR^{13}R^{14}$, —$NR^{13}CO_2R^{14}$, —$CONR^{13}R^{14}$, or —$CH(OH)C(R^{13})_3$;

$R^2$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{15}$, $CH_2NR^{15}R^{16}$, —$CH_2OH$, —$NO_2$, $C_3$-$C_6$ cycloalkyl, —$NR^{15}R^{16}$, —$NR^{15}COR^{16}$, —$NHSO_2R$, —$COR^{15}$, —$CO_2R^{15}$, —$OR^{15}$, —$OC_2H_4OR^{15}$, —$SR^{15}$, —$S(O)_nR^{15}$, —$S(O)_nNR^{15}R^{16}$, —$CH(OH)R^{15}$, —$CH_2COR^{15}$, —$OC(O)R^{15}$, —$OCHR^{15}CO_2R^{16}$, —$OCHR^{15}COR^{16}$, —$NR^{15}CONR^{15}R^{16}$, —$NR^{15}CO_2R^{16}$, —$CONR^{15}R^{16}$, or —$CH(OH)C(R^{15})_3$;

$R^3$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{17}$, $CH_2NR^{17}R^{18}$, —$CH_2OH$, —$NO_2$, $C_3$-$C_6$ cycloalkyl, —$NR^{17}R^{18}$, —$NR^{17}COR^{18}$, —$NHSO_2R$, —$COR^{17}$, —$CO_2R^{17}$, —$OR^{17}$, —$OC_2H_4OR^{17}$, —$SR^{17}$, —$S(O)_nR^{17}$, —$S(O)_nNR^{17}R^{18}$, —$CH(OH)R^{17}$, —$CH_2COR^{17}$, —$OC(O)R^{17}$, —$OCHR^{17}CO_2R^{18}$, —$OCHR^{17}COR^{18}$, —$NR^{17}CONR^{17}R^{18}$, —$NR^{17}CO_2R^{18}$, —$CONR^{17}R^{18}$, or —$CH(OH)C(R^{17})_3$;

each $R^4$ and $R^5$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{19}$, $CH_2NR^{19}R^{20}$, —$CH_2OH$, —$NO_2$, $C_3$-$C_6$ cycloalkyl, —$NR^{19}R^{20}$, —$NR^{19}COR^{20}$, —$NHSO_2R$, —$COR^{19}$, —$CO_2R^{19}$, —$OR^{19}$, —$OC_2H_4OR^{19}$, —$SR^{19}$, —$S(O)_nR^{19}$, —$S(O)_nNR^{19}R^{20}$, —$CH(OH)R^{19}$, —$CH_2COR^{19}$, —$OC(O)R^{19}$, —$OCHR^{19}CO_2R^{20}$, —$OCHR^{19}COR^{20}$, —$NR^{19}CONR^{19}R^{20}$, —$NR^{19}CO_2R^{20}$, —$CONR^{19}R^{20}$, or —$CH(OH)C(R^{19})_3$;

$R^6$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{21}$, $CH_2NR^{21}R^{22}$, —$CH_2OH$, —$NO_2$, $C_3$-$C_6$ cycloalkyl, —$NR^{21}R^{22}$, —$NR^{21}COR^{22}$, —$NHSO_2R$, —$COR^{21}$, —$CO_2R^{21}$, —$OR^{21}$, —$OC_2H_4OR^{21}$, —$SR^{21}$, —$S(O)_nR^{21}$, —$S(O)_nNR^{21}R^{22}$, —$CH(OH)R^{21}$, —$CH_2COR^{21}$, —$OC(O)R^{21}$, —$OCHR^{21}CO_2R^{22}$, —$OCHR^{21}COR^{22}$, —$NR^{21}CONR^{21}R^{22}$, —$NR^{21}CO_2R^{22}$, —$CONR^{21}R^{22}$, or —$CH(OH)C(R^{21})_3$;

each $R^7$, $R^8$ and $R^9$ is, independently, H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{23}$, $CH_2NR^{23}R^{24}$, —$CH_2OH$, —$NO_2$, $C_3$-$C_6$ cycloalkyl, —$NR^{23}R^{24}$, —$NR^{23}COR^{24}$, —$NHSO_2R$, —$COR^{23}$, —$CO_2R^{23}$, —$OR^{23}$, —$OC_2H_4OR^{23}$, —$SR^{23}$, —$S(O)_nR^{23}$, —$S(O)_nNR^{23}R^{24}$, —$CH(OH)R^{23}$, —$CH_2COR^{23}$, —$OC(O)R^{23}$, —$OCHR^{23}CO_2R^{24}$, —OCHR²³COR²⁴, —NR²³CONR²³R²⁴, —NR²³CO₂R²⁴, —CONR²³R²⁴, or —CH(OH)C(R²³)₃;

each R¹⁰ is, independently, H, halogen, C₁-C₆ alkyl, C₁-C₆ haloalkyl, C₃-C₆ cycloalkyl, C₂-C₆ alkenyl, C₂-C₆ alkynyl, C₁-C₆ alkoxy, C₁-C₆ haloalkoxy, aryl, heteroaryl or heterocyclyl, —CN, —CH₂CN, —CH₂OR²³, CH₂NR²³R²⁴, —CH₂OH, —NO₂, C₃-C₆ cycloalkyl, —NR²³R²⁴, —NR²³COR²⁴, —NHSO₂R, —COR²³, —CO₂R²³, —OR²³, —OC₂H₄OR²³, —SR²³, —S(O)ₙR²³, —S(O)ₙNR²³R²⁴, —CH(OH)R²³, —CH₂COR²³, —OC(O)R²³, —OCHR²³CO₂R²⁴, —OCHR²³COR²⁴, —NR²³CONR²³R²⁴, —NR²³CO₂R²⁴, —CONR²³R²⁴, or —CH(OH)C(R²³)₃, wherein each alkyl, haloalkyl, or cycloalkyl is optionally substituted with one or more groups independently selected from halogen, hydroxyl, or —CN;

each R¹¹ and R¹² is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R¹³ and R¹⁴ is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R¹⁵ and R¹⁶ is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R¹⁷ and R¹⁸ is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R¹⁹ and R²⁰ is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R²¹ and R²² is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

each R²³ and R²⁴ is, independently, H, —NH₂, C₁-C₆ alkyl, C₁-C₆ haloalkyl, C₃-C₆ cycloalkyl, aryl, heteroaryl or heterocyclyl, where each alkyl, haloalkyl, or cycloalkyl is optionally substituted with one or more groups independently selected from halogen, hydroxyl, or —CN;

Ar is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl 3,4-dihydro-2H-benzo[1,4]oxazine, benzo[1,3]dioxole, or heterocyclyl wherein said Ar is optionally substituted with 1 to 5 R¹⁰;

n is 0-2;

aryl is phenyl, benzyl or naphthyl, each optionally substituted with 1 to 10 substituents independently selected at each occurrence from H, halogen, C₁-C₆ alkyl, C₁-C₆ haloalkyl, C₂-C₆ alkenyl, C₂-C₆ alkynyl, —CN, —NO₂, —CH₂OH, C₃-C₆ cycloalkyl, —NR¹¹R¹², —NR¹¹COR¹², —COR¹¹, —CO₂R¹¹, —OR¹¹, —SR¹¹, —S(O)ₙR¹¹, —CH(OH)R¹¹, —CH₂COR¹¹, —OC(O) R¹¹, —NR¹¹CONR¹¹R¹², —NR¹¹CO₂R¹², —CONR¹¹R¹², and —CH(OH)C(R¹¹)₃;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 10 substituents independently selected at each occurrence from H, halogen, C₁-C₆ alkyl, C₁-C₆ haloalkyl, C₂-C₆ alkenyl, C₂-C₆ alkynyl, —CN, —NO₂, —CH₂OH, C₃-C₆ cycloalkyl, —NR¹¹R¹², —NR¹¹COR¹², —COR¹¹, —CO₂R¹¹, —OR¹¹, —SR¹¹, —S(O)ₙR¹¹, —CH(OH)R¹¹, —CH₂COR¹¹, —OC(O) R¹¹, —NR¹¹CONR¹¹R¹², —NR¹¹CO₂R¹², —CONR¹¹R¹², and —CH(OH)C(R¹¹)₃; and heterocyclyl is optionally substituted with 1 to 10 substituents independently selected at each occurrence from H, halogen, C₁-C₆ alkyl, C₁-C6 haloalkyl, C₂-C₆ alkenyl, C₂-C6 alkynyl, —CN, —NO₂, —CH₂OH, C₃-C₆ cycloalkyl, —NR¹¹R¹², —NR¹¹COR¹², —COR¹¹, —CO₂R¹¹, —OR¹¹, —SR¹¹, —S(O)ₙR¹¹, —CH(OH) R¹¹, —CH₂COR¹¹, —OC(O)R¹¹, —NR¹¹CONR¹¹R¹², —NR¹¹CO₂R¹², —CONR¹¹R¹², and —CH(OH)C(R¹¹)₃.

The present invention further includes compounds of Formula (IC):

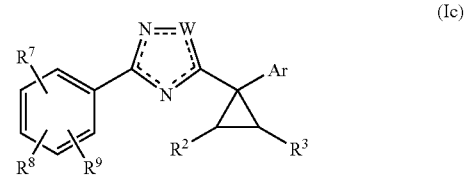

(Ic)

or a pharmaceutically acceptable salt forms thereof, wherein:

W is CR⁶, NR⁶,

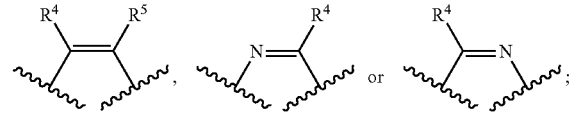

R² is H, halogen, aryl, heteroaryl, heterocyclyl, C₁-C₆ alkyl, C₁-C₆ haloalkyl, C₂-C₆ alkenyl, C₂-C₆ alkynyl, —CN, —CH₂CN, —CH₂OR¹⁵, CH₂NR¹⁵R¹⁶, —CH₂OH, —NO₂, C₃-C₆ cycloalkyl, —NR¹⁵R¹⁶, —NR¹⁵COR¹⁶, —NHSO₂R, —COR¹⁵, —CO₂R¹⁵, —OR¹⁵, —OC₂H₄OR¹⁵, —SR¹⁵, —S(O)ₙR¹⁵, —S(O)ₙNR¹⁵R¹⁶, —CH(OH)R¹⁵, —CH₂COR¹⁵, —OC(O)R¹⁵, —OCHR¹⁵CO₂R¹⁶, —OCHR¹⁵COR¹⁶, —NR¹⁵CONR¹⁵R¹⁶, —NR¹⁵CO₂R¹⁶, —CONR¹⁵R¹⁶, and —CH(OH)C(R¹⁵)₃;

R³ is H, halogen, aryl, heteroaryl, heterocyclyl, C₁-C₆ alkyl, C₁-C₆ haloalkyl, C₂-C₆ alkenyl, C₂-C₆ alkynyl, —CN, —CH₂CN, —CH₂OR¹⁷, CH₂NR¹⁷R¹⁸, —CH₂OH, —NO₂, C₃-C₆ cycloalkyl, —NR¹⁷R¹⁸, —NR¹⁷COR¹⁸, —NHSO₂R, —COR¹⁷, —CO₂R¹⁷, —OR¹⁷, —OC₂H₄OR¹⁷, —SR¹⁷, —S(O)ₙR¹⁷, —S(O)ₙNR¹⁷R¹⁸, —CH(OH)R¹⁷, —CH₂COR¹⁷, —OC(O)R¹⁷, —OCHR¹⁷CO₂R¹⁸, —OCHR¹⁷COR¹⁸, —NR¹⁷CONR¹⁷R¹⁸, —NR¹⁷CO₂R¹⁸, —CONR¹⁷R¹⁸, or —CH(OH)C(R¹⁷)₃;

each R⁴ and R⁵ is, independently, H, halogen, aryl, Is heteroaryl, heterocyclyl, C₁-C₆ alkyl, C₁-C₆ haloalkyl, C₂-C₆ alkenyl, C₂-C6 alkynyl, —CN, —CH₂CN, —CH$_2$OR$^{19}$, CH$_2$NR$^{19}$R$^{20}$, —CH$_2$OH, —NO$_2$, C$_3$-C$_6$ cycloalkyl, —NR$^{19}$R$^{20}$, —NR$^{19}$COR$^{20}$, —NHSO$_2$R, —COR$^{19}$, —CO$_2$R$^{19}$, —OR$^{19}$, —OC$_2$H$_4$OR$^{19}$, —SR$^{19}$, —S(O)$_n$R$^{19}$, —S(O)$_n$NR$^{19}$R$^{20}$, —CH(OH)R$^{19}$, —CH$_2$COR$^{19}$, —OC(O)R$^{19}$, —OCHR$^{19}$CO$_2$R$^{20}$, —OCHR$^{19}$COR$^{20}$, —NR$^{19}$CONR$^{19}$R$^{20}$, —NR$^{19}$CO$_2$R$^{20}$, —CONR$^{19}$R$^{20}$, or —CH(OH)C(R$^{19}$)$_3$;

R$^6$ is H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{21}$, CH$_2$NR$^{21}$R$^{22}$, —CH$_2$OH, —NO$_2$, C$_3$-C$_6$ cycloalkyl, —NR$^{21}$R$^{22}$, —NR$^{21}$COR$^{22}$, —NHSO$_2$R, —COR$^{21}$, CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^7$, R$^8$ and R$^9$ is, independently, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{23}$, CH$_2$NR$^{23}$R$^{24}$, —CH$_2$OH, —NO$_2$, C$_3$-C$_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$;

each R$^{10}$ is, independently, H, halogen, C$_1$-C$_6$ alkyl, C$_1$-C$_6$ haloalkyl, C$_3$-C$_6$ cycloalkyl, C$_2$-C$_6$ alkenyl, C$_2$-C$_6$ alkynyl, C$_1$-C$_6$ alkoxy, C$_1$-C$_6$ haloalkoxy, aryl, heteroaryl or heterocyclyl, —CN, —CH$_2$CN, —CH$_2$OR$^{23}$, CH$_2$NR$^{23}$R$^{24}$, —CH$_2$OH, —NO$_2$, C$_3$-C$_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$, wherein each alkyl, haloalkyl, or cycloalkyl is optionally substituted with one or more groups independently selected from halogen, hydroxyl, or —CN;

each R$^{11}$ and R$^{12}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{13}$ and R$^{14}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{17}$ and R$^{18}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{17}$ and R$^{18}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{19}$ and R$^{20}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{21}$ and R$^{22}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{23}$ and R$^{24}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

Ar is of phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl 3,4-dihydro-2H-benzo[1,4]oxazine, benzo[1,3] dioxole, or heterocyclyl wherein said Ar is optionally substituted with 1 to 5 R$^{10}$;

n is 0-2;

aryl is phenyl, benzyl or naphthyl, each optionally substituted with 1 to 10 substituents independently selected at each occurrence from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, or indazolyl, each optionally substituted with 1 to 10 substituents independently selected at each occurrence from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$; and heterocyclyl is optionally substituted with 1 to 10 substituents independently selected at each occurrence from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$.

Further embodiments include compounds of Formula (Id):

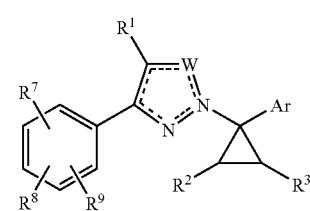

(Id)

or a pharmaceutically acceptable salt forms thereof, wherein:

W is CR$^6$;

R$^1$ is H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{13}$, CH$_2$NR$^{13}$R$^{14}$, —CH$_2$OH, —NO$_2$, C$_3$-C$_6$ cycloalkyl, —NR$^{13}$R$^{14}$, —NR$^{13}$COR$^{14}$, —NHSO$_2$R, —COR$^{13}$, —CO$_2$R$^{13}$, —OR$^{13}$, —OC$_2$H$_4$OR$^{13}$, —SR$^{13}$, —S(O)$_n$R$^{13}$, S(O)$_n$NR$^{13}$R$^{14}$, —CH(OH)R$^{13}$, —CH$_2$COR$^{13}$, —OC(O)R$^{13}$, —OCHR$^{13}$CO$_2$R$^{14}$, —OCHR$^{13}$COR$^{14}$, —NR$^{13}$CONR$^{13}$R$^{14}$, —NR$^{13}$CO$_2$R$^{14}$, —CONR$^{13}$R$^{14}$, or —CH(OH)C(R$^{13}$)$_3$;

R$^2$ is H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{15}$, CH$_2$NR$^{15}$R$^{16}$, —CH$_2$OH, —NO$_2$, C$_3$-C$_6$ cycloalkyl, —NR$^{15}$R$^{16}$, —NR$^{15}$COR$^{16}$, —NHSO$_2$R, —COR$^{15}$, —CO$_2$R$^{15}$, —OR$^{15}$, —OC$_2$H$_4$OR$^{15}$, —SR$^{15}$, —S(O)$_n$R$^{15}$, —S(O)$_n$NR$^{15}$R$^{16}$, —CH(OH)R$^{15}$, —CH$_2$COR$^{15}$, —OC(O)R$^{15}$, —OCHR$^{15}$CO$_2$R$^{16}$, —OCHR$^{15}$COR$^{16}$, —NR$^{15}$CONR$^{15}$R$^{16}$, —NR$^{15}$CO$_2$R$^{16}$, —CONR$^{15}$R$^{16}$, or —CH(OH)C(R$^{15}$)$_3$;

R$^3$ is H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{17}$, CH$_2$NR$^{17}$R$^{18}$, —CH$_2$OH, —NO$_2$, C$_3$-C$_6$ cycloalkyl, —NR$^{17}$R$^{18}$, —NR$^{17}$COR$^{18}$, —NHSO$_2$R, —COR$^{17}$, —CO$_2$R$^{17}$, —OR$^{17}$, —OC$_2$H$_4$OR$^{17}$, —SR$^{17}$, —S(O)$_n$R$^{17}$, —S(O)$_n$NR$^{17}$R$^{18}$, —CH(OH)R$^{17}$, —CH$_2$COR$^{17}$, —OC(O)R$^{17}$, —OCHR$^{17}$CO$_2$R$^{18}$, —OCHR$^{17}$COR$^{18}$, —NR$^{17}$CONR$^{17}$R$^{18}$, —NR$^{17}$CO$_2$R$^{18}$, —CONR$^{17}$R$^{18}$, or —CH(OH)C(R$^{17}$)$_3$;

each R$^4$ and R$^5$ is, independently, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{19}$, CH$_2$NR$^{19}$R$^{20}$, —CH$_2$OH, —NO$_2$, C$_3$-C$_6$ cycloalkyl, —NR$^{19}$R$^{20}$, —NR$^{19}$COR$^{20}$, —NHSO$_2$R, —COR$^{19}$, —CO$_2$R$^{19}$ —OR$^{19}$, —OC$_2$H$_4$OR$^{19}$, —SR$^{19}$, —S(O)$_n$R$^{19}$, —S(O)$_n$NR$^{19}$R$^{20}$, —CH(OH)R$^{19}$, —CH$_2$COR$^{19}$, —OC(O)R$^{19}$, —OCHR$^{19}$CO$_2$R$^{20}$, —OCHR$^{19}$COR$^{20}$, —NR$^{19}$CONR$^{19}$R$^{20}$, —NR$^{19}$CO$_2$R$^{20}$, —CONR$^{19}$R$^{20}$, or —CH(OH)C(R$^{19}$)$_3$;

R$^6$ is H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{21}$, CH$_2$NR$^{21}$R$^{22}$, —CH$_2$OH, —NO$_2$, C$_3$-C$_6$ cycloalkyl, —NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$COR$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^7$, R$^8$ and R$^9$ is, independently, H, halogen, aryl, heteroaryl, heterocyclyl, C$_1$-C$_6$ alkyl, C$_1$-C$_6$ haloalkyl, C$_2$-C$_6$ alkenyl, C$_2$-C$_6$ alkynyl, —CN, —CH$_2$CN, —CH$_2$OR$^{23}$, CH$_2$NR$^{23}$R$^{24}$, —CH$_2$OH, —NO$_2$, C$_3$-C$_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$;

each R$^{10}$ is, independently, H, halogen, C$_1$-C$_6$ alkyl, C$_1$-C$_6$ haloalkyl, C$_3$-C$_6$ cycloalkyl, C$_2$-C$_6$ alkenyl, C$_2$-C$_6$ alkynyl, C$_1$-C$_6$ alkoxy, C$_1$-C$_6$ haloalkoxy, aryl, heteroaryl or heterocyclyl, —CN, —CH$_2$CN, —CH$_2$OR$^{23}$, CH$_2$NR$^{23}$R$^{24}$, —CH$_2$OH, —NO$_2$, C$_3$-C$_6$ cycloalkyl, —NR$^{23}$R$^{24}$, —NR$^{23}$COR$^{24}$, —NHSO$_2$R, —COR$^{23}$, —C$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$, wherein each alkyl, haloalkyl, or cycloalkyl is optionally substituted with one or more groups independently selected from to halogen, hydroxyl, or —CN; each R$^{11}$ and R$^{12}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN; each R$^{13}$ and R$^{14}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{15}$ and R$^{16}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{17}$ and R$^{18}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{19}$ and R$^{20}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{21}$ and R$^{22}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{23}$ and R$^{24}$ is, independently, H, —NH$_2$, C$_1$-C$_6$ alkyl, C$_1$-C$_6$ haloalkyl, C$_3$-C$_6$ cycloalkyl, aryl, heteroaryl or heterocyclyl, where each alkyl, haloalkyl, or cycloalkyl is optionally substituted with one or more groups independently selected from halogen, hydroxyl, or —CN;

Ar is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, indazolyl 3,4-dihydro-2H-benzo(1,4)oxazine, benzo[1,3] dioxole, or heterocyclyl, wherein each Ar is optionally substituted with 1 to 5 R$^{10}$;

n is 0-2;

aryl is phenyl, benzyl or naphthyl, each optionally substituted with 1 to 10 substituents independently selected at each occurrence from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, or indazolyl, each optionally substituted with 1 to 10 substituents independently selected at each occurrence from H, halogen, C$_1$-C$_6$ alkyl, C$_1$-C$_6$ haloalkyl, C$_2$-C$_6$ alkenyl, C$_2$-C$_6$ alkynyl, —CN, —NO$_2$, —CH$_2$OH, C$_3$-C$_6$ cycloalkyl, —NR$^{11}$R$^{12}$, —NR$^{11}$COR$^{12}$, —COR$^{11}$, -CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$; and heterocyclyl is optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, -NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$.

Other embodiments include compounds of Formula (Ie):

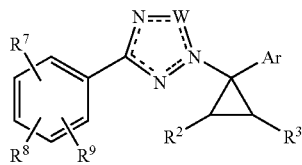

(Ie)

or a pharmaceutically acceptable salt forms thereof, wherein:

W is CR$^6$;

R$^2$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{15}$, CH$_2$NR$^{15}$R$^{16}$, —CH$_2$OH, —NO$_2$, $C_3$-$C_6$ cycloalkyl, —NR$^{15}$R$^{16}$, —NR$^{15}$COR$^{16}$, —NHSO$_2$R, —COR$^{15}$, —CO$_2$R$^{15}$, —OR$^{15}$, —OC$_2$H$_4$OR$^{15}$, —SR$^{15}$, —S(O)$_n$R$^{15}$, —S(O)$_n$NR$^{15}$R$^{16}$, —CH(OH)R$^{15}$, —CH$_2$COR$^{15}$, —OC(O)R$^{15}$, —OCHR$^{15}$CO$_2$R$^{16}$, —OCHR$^{15}$COR$^{16}$, —NR$^{15}$CONR$^{15}$R$^{16}$, —NR$^{15}$CO$_2$R$^{16}$, —CONR$^{15}$R$^{16}$, or —CH(OH)C(R$^{15}$)$_3$;

R$^3$ is H, halogen, aryl, heteroaryl, heterocyclyl, $C_1$-$C_6$ alkyl, $C_1$-$C_6$ haloalkyl, $C_2$-$C_6$ alkenyl, $C_2$-C6 alkynyl, —CN, —CH$_2$CN, —CH$_2$OR$^{17}$, CH$_2$NR$^{17}$R$^{18}$, —CH$_2$OH, —NO$_2$, $C_3$-$C_6$ cycloalkyl, —NR$^{17}$R$^{18}$, —NR$^{17}$COR$^{18}$, —NHSO$_2$R, —COR$^{17}$, —CO$_2$R$^{17}$, —OR$^{17}$, —OC$_2$H$_4$OR$^{17}$, —SR$^{17}$, —S(O)$_n$R$^{17}$, —S(O)$_n$NR$^{17}$R$^{18}$, —CH(OH)R$^{17}$, —CH$_2$COR$^{17}$, —OC(O)R$^{17}$, —OCHR$^{17}$CO$_2$R$^{18}$, —OCHR$^{17}$COR$^{18}$, —NR$^{17}$CONR$^{17}$R$^{18}$, —NR$^{17}$CO$_2$R$^{18}$, —CONR$^{17}$R$^{18}$, or —CH(OH)C(R$^{17}$)$_3$;

each R$^4$ and R$^5$ is, independently, H, halogen, aryl, heteroaryl, heterocyclyl, $C_1$-$C_6$ alkyl, $C_1$-$C_6$ haloalkyl, $C_2$-C6 alkenyl, $C_2$-$C_6$ alkynyl, —CN, —CH$_2$CN, —CH$_2$OR$^{19}$, CH$_2$NR$^{19}$R$^{20}$, —CH$_2$OH, —NO$_2$, $C_3$-$C_6$ cycloalkyl, —NR$^{19}$R$^{20}$, —NR$^{19}$COR$^{20}$, —NHSO$_2$R, —COR$^{19}$, —C$_2$R$^{19}$, —OR$^{19}$, —OC$_2$H$_4$OR$^{19}$, —SR$^{19}$, —S(O)$_n$R$^{19}$, —S(O)$_n$NR$^{19}$R$^{20}$, —CH(OH)R$^{19}$, —CH$_2$COR$^{19}$, —OC(O)R$^{19}$, —OCHR$^{19}$CO$_2$R$^{20}$, —OCHR$^{19}$COR$^{20}$, —NR$^{19}$CONR$^{19}$R$^{20}$, —NR$^{19}$CO$_2$R$^{20}$, CONR$^{19}$R$^{20}$, or —CH(OH)C(R$^{19}$)$_3$;

R$^6$ is H, halogen, aryl, heteroaryl, heterocyclyl, $C_1$-$C_6$ alkyl, $C_1$-$C_6$ haloalkyl, $C_2$-$C_6$ alkenyl, $C_2$-$C_6$ alkynyl, —CN, —CH$_2$CN, —CH$_2$OR$^{21}$, CH$_2$NR$^{21}$R$^{22}$, —CH$_2$OH, —NO$_2$, $C_3$-$C_6$ cycloalkyl, -NR$^{21}$R$^{22}$, —NR$^{21}$COR$^{22}$, —NHSO$_2$R, —COR$^{21}$, —CO$_2$R$^{21}$, —OR$^{21}$, —OC$_2$H$_4$OR$^{21}$, —SR$^{21}$, —S(O)$_n$R$^{21}$, —S(O)$_n$NR$^{21}$R$^{22}$, —CH(OH)R$^{21}$, —CH$_2$COR$^{21}$, —OC(O)R$^{21}$, —OCHR$^{21}$CO$_2$R$^{22}$, —OCHR$^{21}$CO$_2$R$^{22}$, —NR$^{21}$CONR$^{21}$R$^{22}$, —NR$^{21}$CO$_2$R$^{22}$, —CONR$^{21}$R$^{22}$, or —CH(OH)C(R$^{21}$)$_3$;

each R$^7$, R$^8$ and R$^9$ is, independently, selected at each occurrence from a group consisting essentially of H, halogen, aryl, heteroaryl, heterocyclyl, $C_1$-$C_6$ alkyl, $C_1$-$C_6$ haloalkyl, $C_2$-C6 alkenyl, $C_2$-$C_6$ alkynyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$;

each R$^{10}$ is, independently, H, halogen, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy, aryl, heteroaryl or heterocyclyl, —CN, —CH$_2$CN, —CH$_2$OR$^{23}$, CH$_2$NR$^{23}$R$^{24}$, —CH$_2$OH, —NO$_2$, $C_3$-$C_6$ cycloalkyl, —NR$^{23}$R$^{24}$, —NR$^{23}$COR$^{24}$, —NHSO$_2$R, —COR$^{23}$, —CO$_2$R$^{23}$, —OR$^{23}$, —OC$_2$H$_4$OR$^{23}$, —SR$^{23}$, —S(O)$_n$R$^{23}$, —S(O)$_n$NR$^{23}$R$^{24}$, —CH(OH)R$^{23}$, —CH$_2$COR$^{23}$, —OC(O)R$^{23}$, —OCHR$^{23}$CO$_2$R$^{24}$, —OCHR$^{23}$COR$^{24}$, —NR$^{23}$CONR$^{23}$R$^{24}$, —NR$^{23}$CO$_2$R$^{24}$, —CONR$^{23}$R$^{24}$, or —CH(OH)C(R$^{23}$)$_3$, wherein each alkyl, haloalkyl, or cycloalkyl is optionally substituted with one or more groups independently selected from halogen, hydroxyl, or —CN;

each R$^{11}$ and R$^{12}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{13}$ and R$^{14}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{15}$ and R$^{16}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{17}$ and R$^{18}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{19}$ and R$^{20}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{21}$ and R$^{22}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each R$^{23}$ and R$^{24}$ is, independently, H, —NH$_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

Ar is phenyl, benzyl, naphthyl, pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl , pyrazolyl, triazolyl, tetrazolyl, indazolyl 3,4-dihydro-2H-benzo[1,4]oxazine, benzo[1,3] dioxol, or heterocyclyl, wherein said Ar is optionally substituted with 1 to 5 R$^{10}$;

n is 0-2;

aryl is phenyl, benzyl or naphthyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$; and heterocyclyl is optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —NO$_2$, —CH$_2$OH, $C_3$-$C_6$ cycloalkyl, —NR$^{11}$R$^{12}$, —NR$^{11}$COR$^{12}$, —COR$^{11}$, —CO$_2$R$^{11}$, —OR$^{11}$, —SR$^{11}$, —S(O)$_n$R$^{11}$, —CH(OH)R$^{11}$, —CH$_2$COR$^{11}$, —OC(O)R$^{11}$, —NR$^{11}$CONR$^{11}$R$^{12}$, —NR$^{11}$CO$_2$R$^{12}$, —CONR$^{11}$R$^{12}$, and —CH(OH)C(R$^{11}$)$_3$.

In still another embodiment, compounds of this invention are compounds of Formulae (I)-(Ie) and pharmaceutically acceptable salts and pro-drug forms thereof wherein Ar is phenyl optionally substituted with 1 to 5 R$^{10}$ groups independently selected at each occurrence.

In still another embodiment, compounds of this invention are compounds of Formulae (I)-(Ie) and pharmaceutically acceptable salts and pro-drug forms thereof wherein each R$^7$, R$^8$ and R$^9$ is, independently, H, halogen, $C_1$-$C_6$ alkyl, $C_1$-$C_6$ haloalkyl, —CN, —OR$^{23}$, or —S(O)$_n$R$^{23}$.

In still another embodiment, compounds of this invention are compounds of Formulae (I)-(Ie) and pharmaceutically acceptable salts and pro-drug forms thereof wherein each R$^{10}$ is, independently, H, halogen, $C_1$-$C_6$ alkyl, $C_1$-$C_6$ haloalkyl, $C_1$-$C_6$ alkoxy, or $C_1$-$C_6$ haloalkoxy.

In still another embodiment, compounds of this invention are compounds of Formulae (I)-(Ie) and pharmaceutically acceptable salts and pro-drug forms thereof wherein R$^1$ is $C_1$-$C_6$ alkyl.

In still another embodiment, compounds of this invention are compounds of Formulae (I)-(Ie) and pharmaceutically acceptable salts and pro-drug forms thereof wherein R$^2$ is H.

In still another embodiment, compounds of this invention are compounds of Formulae (I)-(Ie) and pharmaceutically acceptable salts and pro-drug forms thereof wherein R$^3$ is H.

The term "alkyl" as used herein is directed to a saturated hydrocarbon group (designated by the formula $C_nH2_{n+1}$) which is straight-chained, branched or cyclized ("cycloalkyl") and which is unsubstituted or substituted, i.e., has had one or more of its hydrogens replaced by another atom or molecule. Commonly used abbreviations have the following meanings: Me is methyl, Et is ethyl, Pr is propyl, Bu is butyl. The prefix "n" means a straight chain alkyl. The prefix "c" means a cycloalkyl. The prefix "(S)" means the S enantiomer and the prefix "(R)" means the R enantiomer. Alkenyl" includes hydrocarbon chains of either a straight or branched configuration and one or more unsaturated carbon-carbon bonds which may occur in any stable point along the chain, such as ethenyl, propenyl, and the like. "Alkynyl" includes hydrocarbon chains of either a straight or branched configuration and one or more triple carbon-carbon bonds which may occur in any stable point along the chain, such as ethynyl, propynyl and the like. "Haloalkyl" is intended to include both branched and straight-chain alkyl having the specified number of carbon atoms, substituted with one or more halogen substituents. Example haloalkyl groups include CF$_3$ and CHF$_2$. "Alkoxy" represents an alkyl group of indicated number of carbon atoms attached through an oxygen bridge and "haloalkoxy" is an alkoxy group substituted with one or more halogen atoms. Example alkoxy groups include methoxy, ethoxy, propoxy and example haloalkoxy groups include OCF$_3$ and OCHF$_2$. "Cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" includes fluoro, chloro, bromo, and iodo.

"Aryl" designates either the 6-carbon benzene ring or the condensed 6-carbon rings of other aromatic derivatives (see, e.g., Hawley's Condensed Chemical Dictionary (13 ed.), R. J. Lewis, ed., J. Wiley & Sons, Inc., New York (1997)). Aryl groups include, without limitation, phenyl, benzyl, naphthyl.

"Heteroaryl" rings are aromatic heterocycles typically containing from about 1-4 heteroatoms (typically O, N or S). Heteroaryl includes, without limitation: pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl and indazolyl.

Substituent groupings, e.g., $C_{1-4}$ alkyl, are known, and are hereby stated, to include each of their individual substituent members, e.g., $C_1$ alkyl, $C_2$ alkyl, $C_3$ alkyl and $C_4$ alkyl.

"Heterocycle" refers to carbocyclic moieties in which one or more (e.g., from about 1 to about 4) ring-forming carbon atoms are replaced with heteroatoms (e.g., O, N, or S). Heterocycles can be saturated or unsaturated. Heterocycles can be aromatic (heteroaryl) or non-aromatic. Heterocycles can also be optionally substituted with 1 to 10 substituents. Examples of heterocyclyl groups include tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, and the like.

"Substituted" means that one or more hydrogen on the designated atom is replaced with a selection from the indicated group, provided that the designated atom's normal valency is not exceeded, and that the substitution results in a stable compound.

"Unsubstituted" atoms bear all of the hydrogen atoms dictated by their valency. When a substituent is keto, then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

In addition to the compounds described and listed hereinabove, this invention provides their corresponding pharmaceutically acceptable salt, radiolabelled, various stereoisomeric and prodrug forms. "Pharmaceutically acceptable salts" of compounds of this invention are also provided herein. The phrase "pharmaceutically acceptable" is employed to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of compounds, suitable for use in contact with the tissues of human beings and animals without excessive toxicity, irritation, allergic response, or other problem or complication, commensurate with a reasonable benefit/risk ratio.

Pharmaceutically acceptable salt forms of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Radiolabelled compounds, i.e. wherein one or more of the atoms described are replaced by a radioactive isotope of that atom (e.g. C replaced by $^{14}$C or by $^{11}$C, and H replaced by $^{3}$H or $^{18}$F), are also provided for herein. Such compounds have a variety of potential uses, e.g. as standards and reagents in determining the ability of a potential pharmaceutical to bind to neurotransmitter proteins, or for imaging compounds of this invention bound to biological receptors in vivo or in vitro.

Many compounds of this invention have one or more asymmetric centers or planes. Unless otherwise indicated, all chiral (enantiomeric and diastereomeric) and racemic forms are included in the present invention. Many geometric isomers of olefins, C═N double bonds, and the like can also be present in the compounds, and all such stable isomers are contemplated in the present invention. The compounds may be isolated in optically active or racemic forms, for example, by chiral chromatography or chemical resolution. It is well known in the art how to prepare optically active forms, such as by resolution of racemic forms or by synthesis from optically active starting materials. All chiral, (enantiomeric and diastereomeric) and racemic forms and all geometric isomeric forms or a structure are intended, unless the specific stereochemistry or isomer form is specifically indicated.

"Prodrugs" are considered to be any covalently bonded carriers which release the active parent drug of Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of Formula (I) and the like.

The term "therapeutically effective amount" of a compound of this invention means an amount effective to antagonize abnormal level of CRF or treat the symptoms of affective disorder, anxiety or depression in a host.

Also provided herein is a pharmaceutical composition comprising one or more of the above compounds and a pharmaceutically acceptable carrier. Further provided is a method of treating a mammal afflicted with affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis or hypoglycemia which method comprises administering to the mammal a therapeutically effective dose of a pharmaceutical composition provided herein.

Also provided herein are methods of treating a mammal afflicted with a disorder characterized by an abnormal level of CRF comprising administering to the mammal a therapeutically effective amount of any compound of Formulas I and Ia-Ie. In some embodiments the disorder is characterized by elevated levels of CRF. Some example treatable disorders characterized by abnormal levels of CRF include affective disorder, anxiety, depression, headache, irritable bowel syndrome, post-traumatic stress disorder, supranuclear palsy, immune suppression, Alzheimer's disease, gastrointestinal diseases, anorexia nervosa, drug addiction, drug or alcohol withdrawal symptoms, inflammatory diseases, cardiovascular, human immunodeficiency virus infection, hemorrhagic stress, obesity, infertility, head and spinal cord traumas, epilepsy, stroke, ulcers, amyotrophic lateral sclerosis, and hypoglycemia. In some embodiments, the treatable disorder is affective disorder, anxiety or depression.

The compounds provided herein are, for example and without limitation, made by the synthetic routes and schemes set forth hereinbelow.

SYNTHESES

The compounds described in the invention may be prepared by one of the general schemes outlined below in Schemes 1-6b.

Cyclopropane-pyridines are synthesized according to the general scheme shown below (Scheme 1).

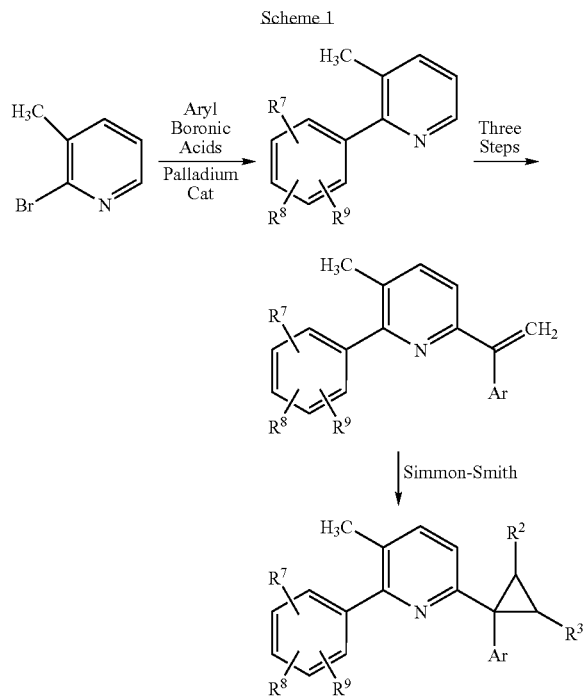

Cyclopropane-pyrimidines are synthesized according to the general scheme shown below (Scheme 2).

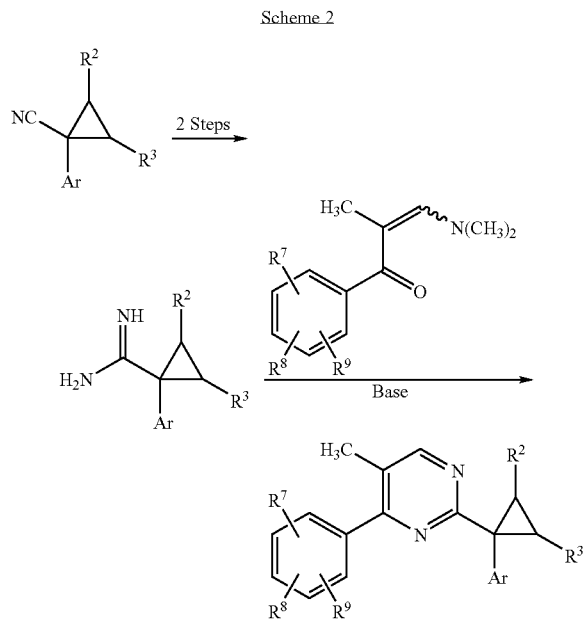

Cyclopropane-pyrazines are synthesized according to the general scheme shown below (Scheme 3).

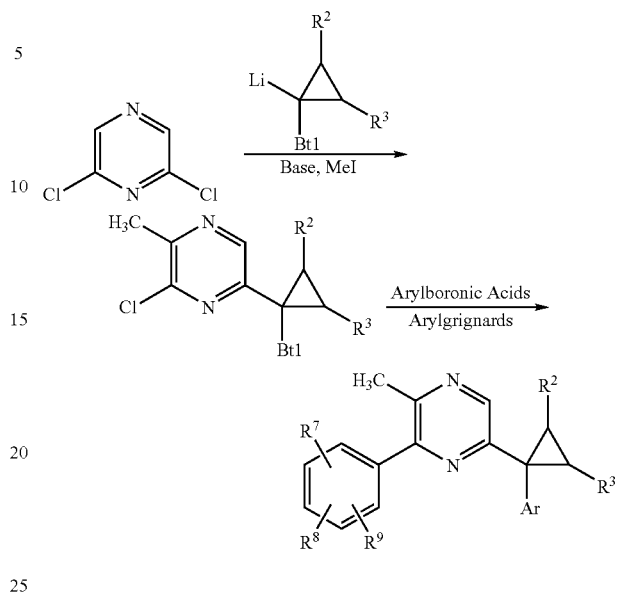

Cyclopropane-pyrazoles can be synthesized according to the general schemes shown below (Scheme 4a, 4b). Fischer E. and Buelow, Chem. Ber; 1885, 2137 and Werner Andreas et al. Tetrahedron, 51, 16, 1995, 4779-4800.

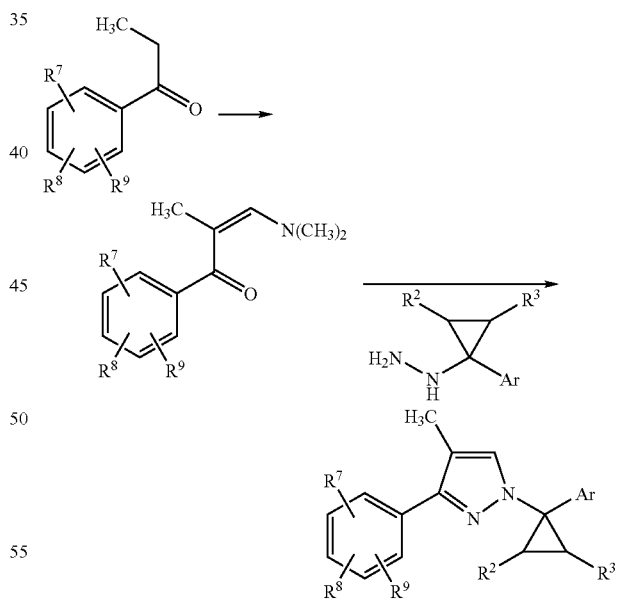

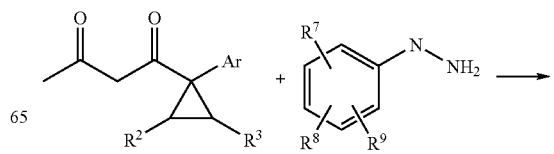

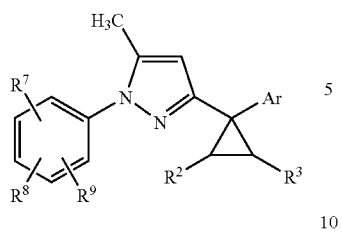

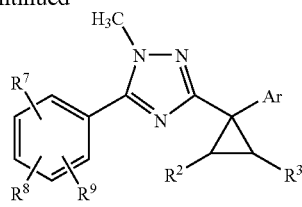

Cyclopropane-imidazoles can be synthesized according to the general scheme shown below (Scheme 5a and 5b) or according to Lantos Ivan et al. J. Org. Chem. 58, 25, 1993, 7092-7095.

Scheme 5a

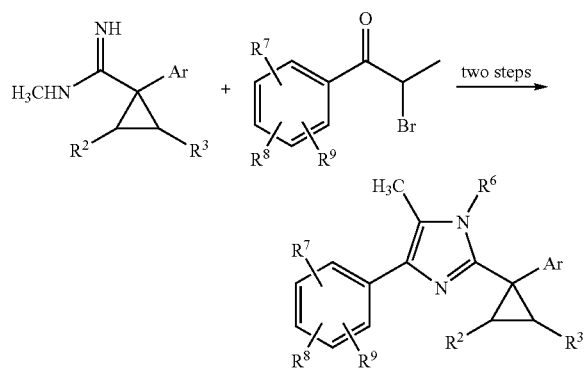

Scheme 5b

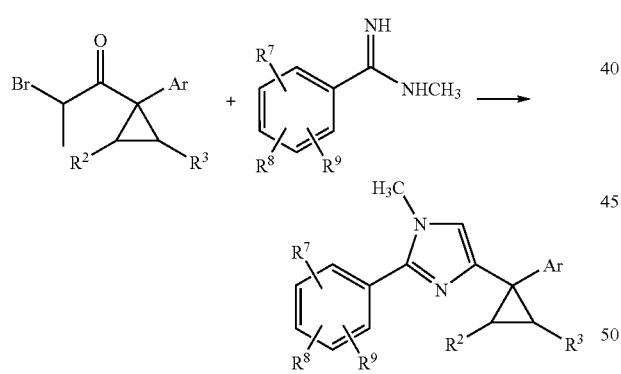

Cyclopropane-triazoles are synthesized according to the general scheme shown below (Scheme 6a and 6b).

Scheme 6a

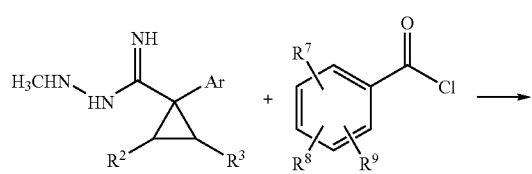

Scheme 6b

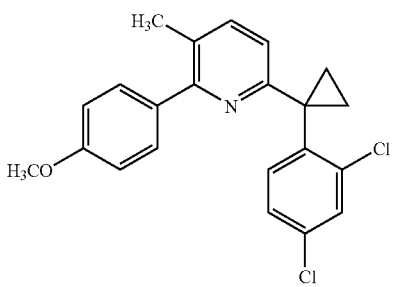

The examples that follow are representative compounds of this invention as well as intermediates thereof and should not be considered as limiting the synthetic scope of the invention which is defined in the appended claims. The synthesis of intermediates in the experimental section is obtained through methods known to those skilled in the art. References are cited within the experimental part.

EXAMPLES

Synthesis of Cyclopropane substituted with Pyridine 2-(4-Methoxy-phenyl)-3-methyl-pyridine A solution of 3-methyl-2-bromopyridine (1.0 mL, 9.0 mmol), DME (32 mL), water (13.5 mL), barium hydroxide octahydrate (8.55 g, 27.1 mmol), 4-methoxyphenylboronic acid (2.76 g, 18.1 mmol) and triphenyl phosphine (0.49 g, 1.87 mmol) was stirred rapidly, and nitrogen was bubbled into the solution for 10 min. Bis[triphenylphosphine]palladium(II) chloride (0.63 g, 0.90 mmol) was added, and the mixture was warmed to 85° C. using an oil bath and stirred for 18 h. The mixture was poured onto ice, and extracted three times with EtOAc. The combined organic extracts were washed with water and saturated aqueous NaCl, dried over $Na_2SO_4$, then filtered and concentrated in vacuo. The crude residue was purified by chromatography on silica gel (85:15 to 70:30 hexanes/EtOAc) to provide compound 1 (1.5 g, 84%) as a yellow oil: $^1$H NMR (300 MHz, CDCl$_3$) δ8.51 (dd, J=4.8, 1.2 Hz, 1 H), 7.56 (d, J=7.1 Hz, 1 H), 7.46-7.51 (m, 2H), 7.14 (dd, J=7.6, 4.8 Hz, 1 H), 6.95-7.01 (m, 2 H), 3.86 (s, 3 H), 2.37 (s, 3 H); ESI MS m/z=200 [C$_{13}$H$_{13}$NO+H]$^+$.

(2,4-Dichloro-phenyl)-[6-(4-methoxy-phenyl)-5-methyl-pyridin-2-yl]-methanol

To a solution of pyridine 1 (500 mg, 2.52 mmol) in THF (5 mL) was added t-butyllithium (1.7 M in pentane, 1.63 mL, 2.77 mmol) at –78° C. The reaction mixture was stirred at –78° C. for 1 h and then 2,4-dichlorobenzaldehyde (530 mg, 3.02 mmol) in THF (5 mL) was added dropwise. The mixture was stirred at –78° C. for 2 h and then treated with saturated aqueous NH$_4$Cl. The organic layer was separated and the aqueous layer was extracted (3 x) with EtOAc. The combined organic layers were washed with brine, dried over Na$_2$SO$_4$, filtered and concentrated in vacuo. The residue was purified by chromatography on silica gel (67:33 hexanes/EtOAc) to provide alcohol 2 (290 mg, 31%) as colorless oil: $^1$H NMR (300 MHz, CDCl$_3$) δ 7.53 (d, J=6.8 Hz, 2 H), 7.49 (d, J=7.9 Hz, 1 H), 7.40 (d, J=2.0 Hz, 1 H), 7.36 (d; J=8.5 Hz, 1 H), 7.19 (dd, J=7.9, 2.0 Hz, 1 H), 7.00-7.04 (m, 3 H), 6.21 (d, J=4.0 Hz, 1 H), 5.90 (d, J=4.0 Hz, 1 H), 3.88 (s, 3 H), 2.37 (s, 3 H); ESI MS m/z=374 [C$_{20}$H$_{17}$Cl$_2$NO$_2$+H]$^+$.

(2,4-Dichloro-phenyl)-[6-(4-methoxy-phenyl)-5-methyl-pyridin-2-yl]-methanone

A mixture of alcohol 2 (284 mg, 0.76 mmol), MnO$_2$ (660 mg, 7.6 mmol), and toluene (10 mL) was heated at 100° C. under N$_2$ for 1 h and then cooled to room temperature. The reaction mixture was filtered through a pad of silica gel. The filtrate was concentrated in vacuo and the residue was purified by chromatography on silica gel (80:20 hexanes/EtOAc) to provide target 3 (260 mg, 92%) as a light yellow oil: $^1$H NMR (300 MHz, CDCl$_3$) δ 7.98 (d, J=7.8 Hz, 1 H), 7.75 (d, J=7.8 Hz, 1 H), 7.28-7.50 (m, 5 H), 6.93 (d, J=8.6 Hz, 2 H), 3.84 (s, 3 H), 2.48 (s, 3 H); ESI MS m/z=372 [C$_{20}$H$_{15}$Cl$_2$NO$_2$+H]$^+$; IR (film) 2965, 2837, 1678, 1609, 1584, 1514, 1455, 1314, 1249, 1176, 1104, 1030 cm$^{-1}$; HPLC 97.2%, t$_r$=16.93 min.

6-[1-(2,4-Dichloro-phenyl)-vinyl]-2-(4-methoxy-phenyl)-3-methyl-pyridine

To a mixture of methyltriphenylphosphonium bromide (204 mg, 0.57 mmol) and THF (4 mL) was added n-BuLi (1.6 M in hexanes, 0.4 mL, 0.63 mmol) dropwise at room temperature. The mixture was stirred under nitrogen as the solid dissolved. Ketone 3 (212 mg, 0.57 mmol) in THF (4 mL) was added dropwise at room temperature, and the mixture was stirred under N$_2$ overnight. The reaction mixture was filtered through a pad of silica gel. The filtrate was concentrated in vacuo and the residue was purified by chromatography on silica gel (80:20 hexanes/EtOAc) to provide target 4 (172 mg, 82%) as colorless oil: $^1$H NMR (300 MHz, CDCl$_3$) δ 7.55 (d, J=8.7 Hz, 2 H), 7.44 (m, 2 H), 7.28 (m, 2 H), 6.96 (d, J=8.7 Hz, 2 H), 6.80 (d, J=7.9 Hz, 1 H) , 6.55 (d, J=1.7 Hz, 1 H), 5.55 (d, J=1.7 Hz, 1 H), 3.85 (s, 3 H), 2.37 (s, 3 H); APCI MS m/z=370 [C$_{21}$H$_{17}$Cl$_2$NO+H]$^+$; IR (ATR) 2918, 1609, 1585, 1513, 1461, 1247, 1175, 1092 cm$^{-1}$; HPLC >99%, t$_r$=15.58 min.

6-[1-(2,4-Dichloro-phenyl)-cyclopropyl]-2-(4-methoxy-phenyl)-3-methyl-pyridine

To a solution of alkene 4 (85 mg, 0.23 mmol) in 1,2-dichloroethane (2 mL) was added diethylzinc (1.0 M in hexanes, 1.15 mL, 1.15 mmol) at 0° C. Chloroiodomethane (0.17 mL, 2.3 mmol) was added dropwise, and then the reaction mixture was stirred at 0° C. under N$_2$ for 30 min. The reaction mixture was heated at reflux under N$_2$ for 4 h. The reaction mixture was cooled to room temperature, diluted with EtOAc, and treated with saturated aqueous NH$_4$Cl. The organic layer was separated, and the aqueous layer was extracted (2 x) with EtOAc. The combined organic layers were washed with brine, dried over Na$_2$SO$_4$, filtered and concentrated in vacuo. The residue was purified by chromatography on silica gel (90:10 hexanes/EtOAc) to provide target 5 (25 mg, 28%) as colorless oil: $^1$H NMR (300 MHz, CDCl$_3$) δ 7.53 (d, J=8.7 Hz, 2 H), 7.43 (m, 2 H), 7.28 (m, 2 H), 6.96 (d, J=8.7 Hz, 2 H), 6.51 (d, J=7.9 Hz, 1 H), 3.86 (s, 3 H), 2.31 (s, 3 H), 1.87 (dd, J=6.8, 3.8 Hz, 2 H), 1.23 (dd, J=6.8, 3.8 Hz, 2 H); APCI MS m/z=384 [C$_{22}$H$_{19}$Cl$_2$NO+H]$^+$; IR (ATR) 2954, 2927, 1608, 1588, 1514, 1462, 1247, 1174 cm$^{-1}$; HPLC 97.4%, t$_r$=16.30 min.

Synthesis of Cyclopropane substituted with Pyrimidine

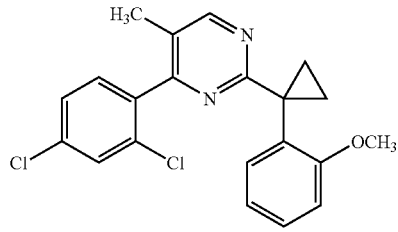

1-(2-Methoxy-phenyl)-cyclopropanecarbonitrile

A mixture of 2-fluoroanisole (1.78 mL, 15.9 mmol), cyclopropanecarbonitrile (4.68 mL, 63.6 mmol), and KHMDS (0.5 M solution in toluene, 50 mL, 24 mmol) was stirred and heated to 60° C. under N$_2$. After 5 h, the mixture was allowed to cool to room temperature, then treated with 1 N HCl and extracted twice with toluene. The toluene extracts were combined, washed with brine, dried over Na$_2$SO$_4$, filtered, and the solvent was removed in vacuo. The oily residue was dissolved in CH$_2$Cl$_2$ and purified by chromatography on silica gel (gradient 3:1 hexanes/CH$_2$Cl$_2$ to CH$_2$Cl$_2$) to provide compound 6 (530 mg, 21%) as a clear, colorless oil: $^1$H NMR (300 MHz, CDCl$_3$) δ 7.19-7.34 (m, 2 H), 6.88-6.93 (m, 2 H), 3.93 (s, 3 H), 1.58-1.63 (m, 2 H), 1.23-1.27 (m, 2 H).

1-(2-Methoxy-phenyl)-cyclopropanecarboximidic acid ethyl ester

A solution of compound 6 (215 mg, 1.33 mmol) in anhydrous EtOH (15 mL) was stirred and cooled to 0° C. under N$_2$. Anhydrous HCl (g) was bubbled into the solution until it was apparently saturated (approximately 8 min) . The flask was stoppered well and allowed to warm to room temperature overnight, while stirring slowly. The solvent was removed in vacuo, and the sample was placed under reduced pressure for 3 h to provide compound 7 (quantitative yield) as a clear, light yellow gum: $^1$H NMR (300 MHz, DMSO-d$_6$) δ7.39 (t, J=7.5 Hz, 1 H), 7.28 (d, J=7.5 Hz, 1 H), 7.07 (d, J=8.1 Hz, 1 H), 6.97 (t, J=7.4 Hz, 1 H), 4.35-4.41 (m, 2 H), 3.80 (S, 3 H), 1.79 (br s, 2 H), 1.41 (br s, 2 H), 1.27 (t, J=6.9 Hz, 3 H).

1-(2 -Methoxy-phenyl)-cyclopropanecarboxamidine

Compound 7 [290 mg (estimated), 1.33 mmol] was stirred as a solution of NH$_3$ (2.0 M in MeOH; 10 mL, 40 mmol) was added slowly, causing a white precipitate to form rapidly. The mixture was stirred for 3 h at room temperature under N$_2$, then heated to 60° C. and stirred overnight under N$_2$. The solvent was removed in vacuo and the sample was placed under reduced pressure for 3 h to provide compound 8 (374 mg; theoretical yield=253 mg; note, the sample was contaminated with NH$_4$Cl as determined by $^1$H NMR spectral analysis) as a yellow solid: $^1$H NMR (300 MHz, CD$_3$OD) δ 7.35-7.41 (m, 2 H), 6.97-7.06 (m, 2 H), 3.89 (s, 3 H), 1.62-1.67 (m, 2 H), 1.35-1.40 (m, 2 H); ESI MS m/z=191 [C$_{11}$H$_{14}$N$_2$O+H]$^+$.

1-(2,4-Dichloro-phenyl)-3-dimethylamino-2-methyl-propenone

A mixture of compound 9 (5.0 g, 25 mmol) and N,N-dimethylformamide dimethyl acetal (4.9 mL, 37 mmol) was stirred under N$_2$ and heated to reflux overnight, then allowed to cool to room temperature and stirred for 2 d. Water was added to the mixture, which was then extracted three times with Et$_2$O. The organic layers were combined and washed with brine, dried over Na$_2$SO$_4$, filtered, and the solvent removed in vacuo to provide a dark brown oily residue. This residue was dissolved in CH$_2$Cl$_2$ and purified by chromatography on silica gel (gradient 2:1 to 1:1 hexanes/EtOAc) to provide compound 10 (3.52 g, 55%) as a dark brown, viscous oil which solidified on standing: $^1$H NMR (300 MHz, CDCl$_3$) δ 7.37 (d, J=1.8 Hz, 1 H), 7.22-7.25 (m, 1 H), 7.13-7.16 (m, 1 H), 6.65 (br s, 1 H), 3.07 (s, 6 H), 2.12 (s, 3 H); ESI MS m/z=258 [C$_{12}$H$_{13}$Cl$_2$NO+H]$^+$.

4-(2,4-Dichloro-phenyl)-2-[1-(2-methoxy-phenyl)-cyclopropyl]-5-methyl-pyrimidine Compound 8 (180 mg, 0.95 mmol) was dissolved in EtOH (3 mL) and stirred under N$_2$. The reaction mixture was cooled to 0° C. and NaOEt (190 mg, 2.80 mmol) was added. The mixture was stirred for 20 min at 0° C., then compound 10 (245 mg, 0.95 mmol) was added, as a solution in EtOH (2 mL). The reaction mixture was allowed to warm to room temperature and stirred overnight. Another portion of NaOEt (80 mg, 1.2 mmol) was added and the mixture was heated at reflux for 1.5 h. After allowing to cool to room temperature, the mixture was diluted with CH$_2$Cl$_2$, washed with brine, dried over Na$_2$SO$_4$, filtered, and the solvent removed in vacuo. The light brown oily residue was dissolved in CH$_2$Cl$_2$ and purified by chromatography on silica gel (CH$_2$Cl$_2$) to provide target 11 (148 mg, 40%) as a yellow solid: mp 46-48° C.; $^1$H NMR (300 MHz, CDCl$_3$) δ 8.39 (s, 1 H), 7.47 (d, J=1.8 Hz, 1 H), 7.25-7.36 (m, 3 H), 7.18 (d, J=8.2 Hz, 1 H), 6.96 (t, J=7.4 Hz, 1 H), 6.89 (d, J=8.2 Hz, 1 H), 3.73 (s, 3 H), 2.04 (s, 3 H), 1.71-1.74 (m, 2 H), 1.28-1.32 (m, 2 H); APCI MS m/z=385 [C$_{21}$H$_{18}$Cl$_2$N$_2$O+H]$^+$; IR (KBr) 3005, 2934, 2833, 1577, 1495, 1425, 1239, 1084, 1025, 944, 867, 818, 798, 752 cm$^{-1}$; HPLC 98.8% (AUC), t$_r$=16.45 min. Anal. Calcd for C$_{21}$H$_{18}$Cl$_2$N$_2$O: C, 65.46; H, 4.71; N, 7.27. Found: C, 65.12; H, 4.74; N, 6.97.

Synthesis Of Cyclopropane Substituted With Pyrazine

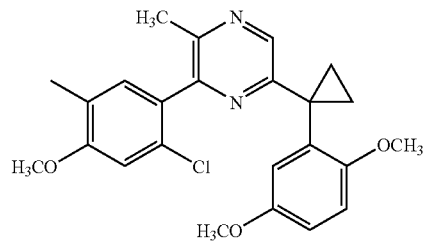

3-Methyl-2,6-dichloropyrazine

Synthesized according to the general procedure given in Walker II, J. A.; Liu, W.; Wise, D. S. Drach, J. C.; Townsend, L. B. et.al. *J. Med. Chem.* 1998, 41, 1236-1241. The mono anion of 2,6-dichloro-pyrazine was generated as described and quenched with 500 mol % MeI to provide a 65% isolated yield of the title compound.

1-(6-Chloro-5-methyl-pyrazin-2-yl)-1H-benzotriazole

To 13 mL of 0.1 M THF solution containing 1-lithio-1-cyclopropyl-1H-benzotriazole (0.13 mmol), prepared according to Katritzky, A. R.; Weihong, D.; Levell, J. R.; Jianqing, L. *J. Org. Chem.*, 1998, 63, 6710-6711, at −78° C. was added 0.20 mL TMEDA (0.13 mmol). To the mixture was added over 20 min 219 mg 3-methyl-2,6-dichloropyrazine in 2.7 mL THF. After stirring 45 min the reaction was quenched with water, then allowed to reach 0° C. before neutralization with HOAC (aq). The reaction mixture was partitioned between diethyl ether and std NaHCO$_3$ and the residue resulting from the aqueous layer was purified by column chromatography with hexane ethyl acetate (0.1% Et$_3$N) to provide 85% yield of the title compound based on converted 1-cyclopropyl-1H-benzotriazole.

2-Chloro-2-methoxy-1-methyl-benzene

5-Chloro-2-methyl-phenol (10 g, 70.1 mmol) was dissolved in 150 ml Acetone. Methyliodide (10.94 g, 77.1 mmol) and K$_2$CO$_3$ (10.65 g, 77.1 mmol) were added and the reaction was stirred at room temperature to provide after work up 2-Chloro-2-methoxy-1-methyl-benzene. (9.65 g, 88%)

1-Bromo-2-chloro-4-methoxy-1-methyl-benzene

2-Chloro-2-methoxy-1-methyl-benzene (1.0 g, 6.4 mmol) was dissolved in Acetonitrile and N-Bromo-succinimid (NBS) (1.25 g, 7.0 mmol) was added. The reaction mixture was purged with Nitrogen and stirred for 12 hours at RT. The solvent was evaporated and the product was isolated by silica gel column chromatography with Ethyl acetate Hexane. (1.35 g, 90%)

1-Bromo-2-Chloro-4-methoxy-5-methyl-phenyl boronic acid

1-Bromo-2-chloro-4-methoxy-1-methyl-benzene (5 g, 31.2 mmol) was dissolved in 60 ml dry THF. The reaction mixture was purged with Nitrogen and cooled to −78° C. n-Butyllithium (1.6 M, 14.6 mL, 23.3 mmol) was added over 10 minutes and the reaction was stirred for an additional 30 minutes. B(OCH$_3$)$_3$ (2.9 ml, 25.4 mmol) was added. The reaction was allowed to warm to room temperature and was stirred for another 12 hours.

The reaction mixture was concentrated and 3 N HCl (70 ml) were added. The reaction mixture was stirred for 6 hours and the organic phase was extracted several times with Ether. The combined organic extracts were washed with 3 N NaOH and acidified to pH 1. The organic phase was then separated dried over Na$_2$CO$_3$ and concentrated in vacuo to provide (2.22 g, 68%) of 1-Bromo-2-Chloro-4-methoxy-5-methyl-phenyl boronic acid 1-[6-(2-Chloro-4-methoxy-5-methyl-phenyl)-5-methyl-pyrazin-2-yl]-1H-benzotriazole To a stirred solution of 83 mg 1-(6-Chloro-5-methyl-pyrazin-2-yl)-1H-benzotriazole (0.29 mmol) and 58 mg 2-chloro-4-methoxy-5-methyl-phenyl boronic acid (0.29 mmol) in 0.3 mL toluene was added 0.29 mL 2 M Na$_2$CO$_3$ (aq). After 10 min 10 mg (pbbp)Pd(Cl)$_2$ was added as a solid and the resulting suspension was heated at 110° C. for 16 h. The organic phase was directly subjected to column chromatography eluting with hexane ethyl acetate (0.1% Et$_3$N) to provide the title compound in 50% yield.

3-(2-Chloro-4-methoxy-5-methyl-phenyl)-5-[1-(2,5-dimethoxy-phenyl)-cyclopropyl]-2-methyl-pyrazine To 46 mg 1-[6-(2-Chloro-4-methoxy-5-methyl-phenyl)-5-methyl-pyrazin-2-yl]-1H-benzotriazole (0.12 mmol) in 200 μL toluene was added 100 μL 0.5 M 2,5-dimethoxyphenyl magnesium bromide in THF. The solution is subjected three times to 3 GHz microwave radiation heating to 150° C. for 15 min. After quenching with saturated ammonium chloride, the organic phase was directly subjected to column chromatography eluting with hexanes DCM followed by hexane ethyl acetate (0.1% Et₃N). Fractions containing the desired product were pooled and concentrated to give a residue that was further purified by RP—HPLC eluting with acetonitrile water (0.03% TFA) giving 2.6 mg of the title compound.

Synthesis Of Cyclopropane Substituted With Imidazol

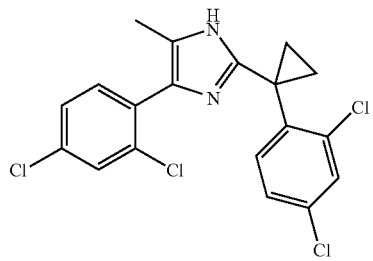

1-(2,4-Dichloro-phenyl)-cyclopropanecarboxamidine 1-(2,4-Dichloro-phenyl)-cyclopropanecarbonitrile (1.06 g, 5 mmol) was dissolved in 4 mL anhydrous MeOH and a solution of HCl (4.0 M in Dioxane; 40 mL). The reaction mixture was stirred for 12 hours and the solvent removed on the rotary evaporator to give crude 1-(2,4-Dichloro-phenyl) cyclopropanecarboximidic acid ethyl ester.

The crude 1-(2,4-Dichloro-phenyl) cyclopropanecarboximidic acid ethyl ester was dissolved in a solution NH₃ (2.0 M in EtOH; 40 mL). Anhydrous NH₃ (g) was bubbled into the solution until it was apparently saturated (60 min). The reaction mixture was stirred for 4 days. The solvent was evaporated and the desired product recrystallized from Ethyl acetate. (350 mg, 31%).

4-(2,4-Dichloro-phenyl)-2-[1-(2,4-dichloro-phenyl)-cyclopropyl]-5-methyl-1H-imidazole 2-Bromo-1-(2,4-dichloro-phenyl)-propane-1-one (28.2 mg, 0.1 mmol), (1-(2,4-Dichloro-phenyl)-cyclopropanecarboxamidine (22.9 mg, 0.1 mmol) and Huenigs Base (20 µl, 0.1 mmol) were dissolved in 1 mL dry DMF and stirred for 12 hours at 85° C. The crude reaction mixture was purified by reversed phase chromatography to provide 4-(2,4-Dichloro-phenyl)-2-[1-(2,4-dichloro-phenyl)-cyclopropyl]-5-methyl-1H-imidazole. (3.9 mg, 9.5%). ESI MS m/z=411.2, 413.2.

Synthesis Of Cyclopropane Substituted With Triazol

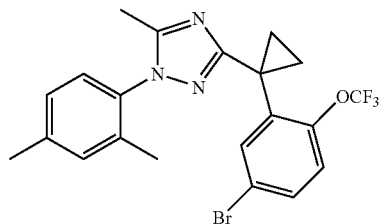

1-(5-Bromo-2-trifuoromethoxy-phenyl)-cyclopropylcarbonitrile

In a flask (3.47 g, 16.6 mmol) of the nitrile was dissolved in Nitromethane (2.69 g, 16.6 mmol) FeCl₃ were added and Br₂ dissolved in Nitromethane was added dropwise under vigorous stirring. The reaction mixture was stirred for an additional 3 h at room temperature. The reaction mixture, water and ether were combined in a seperatory funnel. The organic phase was separated and dried over sodiumsulfate. The crude product was taken into the next step without further purification.

1-(5-Bromo-2-trifuoromethoxy-phenyl)-cyclopropanecarboximidic acid ethyl ester 1-(5-Bromo-2-trifuoromethoxy-phenyl)-cyclopropylcarbonitrile (1.53 g, 5 mmol) was dissolved in 6ml Ethanol. Dioxane (50 ml) was added and the reaction mixture was saturated with HCl (gas). The reaction mixture was stirred for 12 h at RT and then heated to 40° C. for 6 hours. The solvents were evaporated and the crude material was used in the next reaction step without further purification.

3-[1-(5-Bromo-2-trifluoromethoxy-phenyl)-cyclopropyl}-1-(2,4-dimethyl-phenyl)-5-methyl-1-H-[1,2,4]triazole 1-(5-Bromo-2-trifuoromethoxy-phenyl)-cyclopropanecarboximidic acid ethyl ester (35 mg, 0.1 mmol) and (2,4,6-Trimethyl-phenyl)-hydrazine (17.5 mg, 0.1 mmol) were dissolved in 1 ml pyridine. The reaction mixture was stirred for 12 hours. The crude reaction mixture was then treated with Acetyl chloride (0.2 ml) and stirred for 6 hours at 80° C. Saturated NaHCO₃ was added and the reaction mixture was extracted twice with Ethyl acetate to provide 3-[1-(5-Bromo-2-trifluoromethoxy-phenyl)-cyclopropyl}-1-(2,4-dimethyl-phenyl)-5-methyl-1-H-[1,2,4]triazole. (2.2 mg, 4.73%). ESI MS m/z=466.2, 468.2.

TABLE I

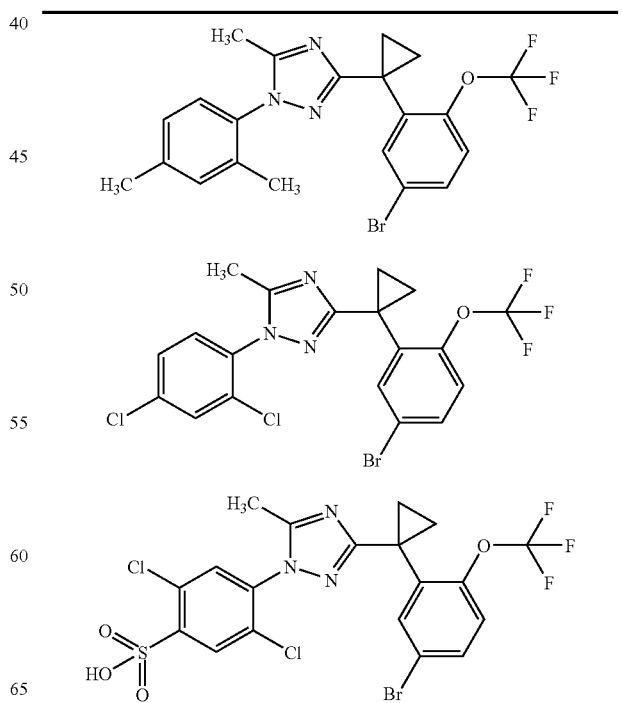

TABLE I-continued

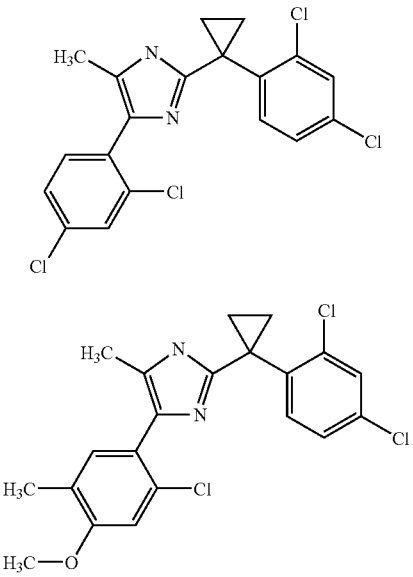

Table I above shows more examples of compounds which may be synthesized using the synthetic routes described herein.

Moreover, in addition to compounds made by these routes and schemes, this invention provides for pharmaceutical compositions comprising pharmaceutically acceptable carriers and therapeutically effective amounts of the compounds. "Pharmaceutically acceptable carriers" are media generally accepted in the art for the delivery of biologically active agents to animals, in particular, mammals. Such media are formulated according to a number of factors well within the purview of those of ordinary skill in the art to determine and account for. These include, without limitation: the type and nature of the active agent being formulated; the subject to which the agent-containing composition is to be administered; the intended route of administration of the composition; and, the therapeutic indication being targeted.

Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., *Remington's Pharmaceutical Sciences*, 17th ed., Mack Publishing Company, Easton, Pa., 1985, the contents of which are incorporated herein by reference.

Compounds provided herein are antagonists of receptors for corticotropin releasing factor ("CRF"), a 41 amino acid peptide that is the primary physiological regulator of pro-opiomelanocortin (POMC)-derived peptide secretion from the anterior pituitary gland [J. Rivier et al., *Proc. Nat. Acad. Sci.* (USA) 80:4851 (1983); W. Vale et al., *Science* 213:1394 (1981)]. Immunohistochemical localization of CRF has also demonstrated that CRF has a broad extrahypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

CRF concentrations have been found to be significantly increased in the cerebral spinal fluid (CSF) of drug-free individuals afflicted with affective disorder or depression [C.B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. Moreover, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)].

CRF produces anxiogenic effects in animals. Moreover, interactions between benzodiazepine/non-benzodiazepine anxiolytics and CRF have been demonstrated in a variety of behavioral anxiety models (D. R. Britton et al., *Life Sci.* 31:363 (1982); C. W. Berridge and A. J. Dunn *Regul. Peptides* 16:83 (1986)]. Preliminary studies using the putative CRF receptor antagonist alpha-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)]. The contents of the above-cited documents are incorporated herein by reference.

Thus, compounds provided herein which, because of their antagonism of CRF receptors, alleviate the effects of CRF overexpression are expected to be useful in treating these and other disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis and hypoglycemia.

This invention thus further provides a method of treating a subject afflicted with a disorder characterized by CRF overexpression, such as those described hereinabove, which comprises administering to the subject a pharmaceutical composition provided herein. Such compositions generally comprise a therapeutically effective amount of a compound provided herein, that is, an amount effective to ameliorate, lessen or inhibit disorders characterized by CRF overexpression. Such amounts typically comprise from about 0.1 to about 1000 mg of the compound per kg of body weight of the subject to which the composition is administered. Therapeutically effective amounts can be administered according to any dosing regimen satisfactory to those of ordinary skill in the art.

Administration is, for example, by various parenteral means. Pharmaceutical compositions suitable for parenteral administration include various aqueous media such as aqueous dextrose and saline solutions; glycol solutions are also useful carriers, and preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents; also used are citric acid and its salts, and EDTA. In addition, parenteral solutions can contain preservatives such as benzalkonium chloride, methyl- or propyl-paraben, and chlorobutanol.

Alternatively, compositions can be administered orally in solid dosage forms, such as capsules, tablets and powders; or in liquid forms such as elixirs, syrups, and/or suspensions. Gelatin capsules can be used to contain the active ingredient and a suitable carrier such as but not limited to lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

UTILITY

CRF-R1 Receptor Binding Assay for the Evaluation of Biological Activity

The following is a description of the isolation of cell membranes containing cloned human CRF-R1 receptors for use in the standard binding assay as well as a description of the assay itself. Messenger RNA was isolated from human hippocampus. The mRNA was reverse transcribed using oligo (dt) 12-18 and the coding region was amplified by PCR from start to stop codons. The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 µM hygromycin. Cells surviving 4 weeks of selection in hygromycin were pooled, adapted to growth in suspension and used to generate membranes for the binding assay described below. Individual aliquots containing approximately 1×108 of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM $MgCl_2$, 2 mM EGTA, 1 µg/l aprotinin, 1 µg/ml leupeptin and 1 µg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 µg/ml to be used in the assay.

Binding assays are performed in 96 well plates; each well having a 300 µl capacity. To each well is added 50 µl of test drug dilutions (final concentration of drugs range from $10^{-10}$-$10^{-5}$ M), 100 µl of $^{125}$I-ovine-CRF ($^{125}$I-o-CRF) (final concentration 150 pM) and 150 µl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, Anal. Biochem. 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris—HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40-60 mg protein). Reactions are initiated by the addition of 1 mM ATP/$^{32}$P] ATP (approximately 2-4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In Vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A compound of Formula (I):

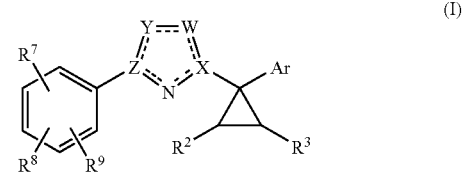

(I)

or a pharmaceutically acceptable salt form thereof, wherein:

W is $NR^6$;

X is C;

Y is $CR^1$;

Z is C;

$R^1$ is H, halogen, aryl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{13}$, $CH_2NR^{13}R^{14}$, —$CH_2OH$, —$NO_2$, $C_3$-$C_6$ cycloalkyl, —$NR^{13}R^{14}$, —$NR^{13}COR^{14}$, —$NHSO_2R$, —$COR^{13}$, —$CO_2R^{13}$, —$OR^{13}$, —$OC_2H_4OR^{13}$, —$SR^{13}$, —$S(O)_nR^{13}$, —$S(O)_nNR^{13}R^{14}$, $CH(OH)R^{13}$, —$CH_2COR^{13}$, —$OC(O)R^{13}$, —$OCHR^{13}CO_2R^{14}$, —$OCHR^{13}COR^{14}$, —$NR^{13}CONR^{13}R^{14}$, —$NR^{13}CO_2R^{14}$, —$CONR^{13}R^{14}$, or —$CH(OH)C(R^{13})_3$;

$R^2$ is H, halogen, aryl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{15}$, $CH_2NR^{15}R^{16}$, —$CH_2OH$, —$NO_2$, $C_3$-$C_6$ cycloalkyl, —$NR^{15}R^{16}$, —$NR^{15}COR^{16}$, —$NHSO_2R$, —$COR^{15}$, —$CO_2R^{15}$, —$OR^{15}$, —$OC_2H_4OR^{15}$, —$SR^{15}$, —$S(O)_nR^{15}$, —$S(O)_nNR^{15}R^{16}$, —$CH(OH)R^{15}$, —$CH_2COR^{15}$, —$OC(O)R^{15}$, —$OCHR^{15}CO_2R^{16}$, —$OCHR^{15}COR^{16}$, —$NR^{15}CONR^{15}R^{16}$, —$NR^{15}CO_2R^{16}$, —$CONR^{15}R^{16}$, or —$CH(OH)C(R^{15})_3$;

$R^3$ is H, halogen, aryl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{17}$, $CH_2NR^{17}R^{18}$, —$CH_2OH$, —$NO_2$, $C_3$-$C_6$ cycloalkyl, —$NR^{17}R^{18}$, —$NR^{17}COR^{18}$, —$NHSO_2R$, —$COR^{17}$, —$CO_2R^{17}$, —$OR^{17}$, —$OC_2H_4OR^{17}$, —$SR^{17}$, —$S(O)_nR^{17}$, —$S(O)_nNR^{17}R^{18}$, —$CH(OH)R^{17}$, —$CH_2COR^{17}$, —$OC(O)R^{17}$, —$OCHR^{17}CO_2R^{18}$, —$OCHR^{17}COR^{18}$, —$NR^{17}CONR^{17}R^{18}$, —$NR^{17}CO_2R^{18}$, —$CONR^{17}R^{18}$, or —$CH(OH)C(R^{17})_3$;

$R^6$ is H, halogen, aryl, $C_1$-$C_6$ alkyl, $C_1$-$C_6$ haloalkyl, $C_2$-$C_6$ alkenyl, $C_2$-$C_6$ alkynyl, —CN, —$CH_2CN$, —$CH_2OR^{21}$, $CH_2NR^{21}R^{22}$, —$CH_2OH$, —$NO_2$, $C_3$-$C_6$ cycloalkyl, —$NR^{21}R^{22}$, —$NR^{21}COR^{22}$, —$NHSO_2R$, —$COR^{21}$, —$CO_2R^{21}$, —$OR^{21}$, $OC_2H_4OR^{21}$, —$SR^{21}$, —$S(O)_nR^{21}$, —$S(O)_nNR^{21}R^{22}$, —$CH(OH)R^{21}$, —$CH_2COR^{21}$, —$OC(O)R^{21}$, —$OCHR^{21}CO_2R^{22}$, —$OCHR^{21}COR^{22}$, —$NR^{21}CONR^{21}R^{22}$, —$NR^{21}CO_2R^{22}$, —$CONR^{21}R^{22}$, or —$CH(OH)C(R^{21})_3$;

each $R^7$, $R^8$ and $R^9$ is, independently, H, halogen, aryl, $C_1$-$C_6$ alkyl, $C_2$-$C_6$ alkenyl, $C_2$-$C_6$ alkynyl, —CN, —$CH_2CN$, —$CH_2OR^{23}$, $CH_2NR^{23}R^{24}$, —$CH_2OH$, —$NO_2$, $C_3$-$C_6$ cycloalkyl, —$NR^{23}R^{24}$, —$NR^{23}COR^{24}$, —$NHSO_2R$, —$COR^{23}$, —$CO_2R^{23}$, —$OR^{23}$, —$OC_2H_4OR^{23}$, —$SR^{23}$, —$S(O)_nR^{23}$, —$S(O)_nNR^{23}R^{24}$, —$CH(OH)R^{23}$, —$CH_2COR^{23}$, —$OC(O)R^{23}$, —$OCHR^{23}CO_2R^{24}$, —$OCHR^{23}COR^{24}$, —$NR^{23}CONR^{23}R^{24}$, —$NR^{23}CO_2R^{24}$, —$CONR^{23}R^{24}$, or —$CH(OH)C(R^{23})_3$;

each $R^{10}$ is, independently, H, halogen, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, $C_1$-$C_6$ alkoxy, $C_1$-$C_6$ haloalkoxy, aryl, heteroaryl or heterocyclyl, —CN, —$CH_2CN$, —$CH_2OR^{23}$, $CH_2NR^{23}R^{24}$, —$CH_2OH$, —$NO_2$, $C_3$-$C_6$ cycloalkyl, —$NR^{23}R^{24}$, —$NR^{23}COR^{24}$, —$NHSO_2R$, —$COR^{23}$, —$CO_2R^{23}$, —$OR^{23}$, —$OC_2H_4OR^{23}$, —$SR^{23}$, —$S(O)_nR^{23}$, —$S(O)_nNR^{23}R^{24}$, —$CH(OH)R^{23}$, —$CH_2COR^{23}$, —$OC(O)R^{23}$, —$OCHR^{23}CO_2R^{24}$, —$OCHR^{23}COR^{24}$, —$NR^{23}CONR^{23}R^{24}$, —$NR^{23}CO_2R^{24}$, —$CONR^{23}R^{24}$, or —$CH(OH)C(R^{23})_3$, wherein each alkyl, haloalkyl, or cycloalkyl is optionally substituted with one or more groups independently selected from halogen, hydroxyl, or —CN;

each $R^{11}$ and $R^{12}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{13}$ and $R^{14}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{15}$ and $R^{16}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{17}$ and $R^{18}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{21}$ and $R^{22}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

each $R^{23}$ and $R^{24}$ is, independently, H, —$NH_2$, $C_1$-$C_6$ alkyl, $C_1$-$C_6$ haloalkyl, $C_3$-$C_6$ cycloalkyl, aryl, heteroaryl or heterocyclyl, where each alkyl, haloalkyl, or cycloalkyl is optionally substituted with one or more groups independently selected from halogen, hydroxyl, or —CN;

Ar is phenyl, benzyl, or naphthyl, wherein said Ar is optionally substituted with 1 to 5 $R^{10}$;

n is 0-2;

aryl is phenyl, benzyl or naphthyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-$C_6$ cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^1R^{12}$, —$NR^{11}CO_2R^{12}$, —$CONR^{11}R^{12}$, and —$CH(OH)C(R^{11})_3$;

heteroaryl is pyridyl, pyrimidinyl, pyrazinyl, pyridazinyl, triazinyl, furanyl, quinolinyl, isoquinolinyl, thienyl, imidazolyl, thiazolyl, indolyl, pyrrolyl, oxazolyl, benzofuranyl, benzothienyl, benzthiazolyl, isoxazolyl, pyrazolyl, triazolyl, tetrazolyl, or indazolyl, each optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-$C_6$ cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^{11}R^{12}$, —$NR^{11}CO_2R^{12}$, —$CONR^{11}R^{12}$, and —$CH(OH)C(R^{11})_3$; and heterocyclyl is optionally substituted with 1 to 10 substituents independently selected at each occurrence from H, halogen, $C_1$-$C_6$ alkyl, $C_1$-$C_6$ haloalkyl, $C_2$-$C_6$ alkenyl, $C_2$-$C_6$ alkynyl, —CN, —$NO_2$, —$CH_2OH$, $C_3$-$C_6$ cycloalkyl, —$NR^{11}R^{12}$, —$NR^{11}COR^{12}$, —$COR^{11}$, —$CO_2R^{11}$, —$OR^{11}$, —$SR^{11}$, —$S(O)_nR^{11}$, —$CH(OH)R^{11}$, —$CH_2COR^{11}$, —$OC(O)R^{11}$, —$NR^{11}CONR^{11}R^{12}$, —$NR^{11}CO_2R^{12}$, —$CONR^{11}R^{12}$, and —$CH(OH)C(R^{11})_3$.

2. The compound of claim 1 wherein Ar is phenyl optionally substituted with 1 to 5 $R^{10}$ groups.

3. The compound of claim 1 wherein each $R^7$, $R^8$ and $R^9$ is, independently, H, halogen, $C_1$-$C_6$ alkyl, —CN, —$OR^{23}$, or —$S(O)_nR^{23}$.

4. The compound of claim 1 wherein each $R^{10}$ is, independently, H, halogen, $C_1$-$C_6$ alkyl, $C_1$-$C_6$ haloalkyl, $C_1$-$C_6$ alkoxy, or $C_1$-$C_6$ haloalkoxy.

5. The compound of claim 1 wherein $R^1$ is $C_1$-$C_6$ alkyl.

6. The compound of claim 1 wherein $R^2$ is H.

7. The compound of claim 1 wherein $R^3$ is H.

8. A pharmaceutical composition comprising the compound of claim 1 and a pharmaceutically acceptable carrier.

* * * * *